(12) United States Patent
Koh et al.

(10) Patent No.: US 9,018,182 B2
(45) Date of Patent: Apr. 28, 2015

(54) TUMOR SPECIFIC PROMOTER AND ONCOLYTIC VIRUS VECTOR COMPRISING THE SAME

(75) Inventors: Daekyung Koh, Yongin-si (KR); Seongtae Yun, Yongin-si (KR); Kyuhyun Lee, Yongin-si (KR); Hong-Kyu Lee, Yongin-si (KR); Mihee Hwang, Yongin-si (KR); Chae-Ok Yun, Seoul (KR); Eui-Cheol Jo, Yongin-si (KR)

(73) Assignees: Green Cross Corporation, Yongin-si (KR); Mogam Biotechnology Research Institute, Yongin-si (KR); Industry-Academic Cooperation Foundation, Yonsei University, Seoul (KR)

( * ) Notice: Subject to any disclaimer, the term of this patent is extended or adjusted under 35 U.S.C. 154(b) by 73 days.

(21) Appl. No.: 13/642,962

(22) PCT Filed: Apr. 26, 2010

(86) PCT No.: PCT/KR2010/002608
§ 371 (c)(1),
(2), (4) Date: Oct. 23, 2012

(87) PCT Pub. No.: WO2011/136400
PCT Pub. Date: Nov. 3, 2011

(65) Prior Publication Data
US 2013/0065952 A1    Mar. 14, 2013

(51) Int. Cl.
*C12N 15/113*    (2010.01)
*A61K 35/76*    (2006.01)

(52) U.S. Cl.
CPC .............. *A61K 35/76* (2013.01); *A61K 35/13* (2013.01); *C12N 2830/008* (2013.01)

(58) Field of Classification Search
CPC .............. A61K 48/00; A61K 2300/00; A61K 2039/505; A61K 38/00; C12N 15/86
See application file for complete search history.

(56) References Cited

U.S. PATENT DOCUMENTS 7,041,654 B2 *  5/2006  Hochberg et al. ........... 514/44 R

FOREIGN PATENT DOCUMENTS

WO    WO 2004035803 A2 *  4/2004

OTHER PUBLICATIONS

Kim et al. "Evaluation of E1B gene-attenuated replicating adenoviruses for cancer gene therapy." Cancer Gene Therapy (2002) 9, pp. 725-736.*
Yoder et al., "New 5' Regions of the Murine and Human Genes for DNA (Cytosine-5)-Methyl Transferase," The Journal of Biological Chemistry, 1996, vol. 271, No. 49, pp. 31092-31097.
Kimura et al., "Transcription of Mouse DNA methyltransferase 1 (Dnmt1) is Regulated by Both E2F-Rb-HDAC-Dependent and -Independent Pathways," Nucleic Acids Research, 2003, vol. 31, No. 12, pp. 3101-3113.
European Patent Office, European Search Report issued in corresponding EP Application No. 10850768.2, dated Aug. 16, 2013.
Kurita, et al. "DNMT1 and DNMT3b silencing sensitizes human hepatoma cells to TRAIL-mediated apoptosis via up-regulation of TRAIL-R2/DR5 and caspase-8", Cancer Science, vol. 101 No. 6: 1431-1439, Jun. 2010.
Korean Intellectual Property Office, Communication dated Mar. 30, 2014 issued in the corresponding Korean Patent Application No. 10-2012-7030936.

* cited by examiner

*Primary Examiner* — Thaian N Ton
*Assistant Examiner* — Titilayo Moloye
(74) *Attorney, Agent, or Firm* — Sughrue Mion, PLLC

(57) ABSTRACT

Provided are tumor-specific promoters, oncolytic virus vectors and a pharmaceutical composition comprising the virus vector. The virus vector comprising the novel tumor-specific promoter shows excellent oncolytic effects on tumor cells, and thus it is useful for treating a cancer.

12 Claims, 37 Drawing Sheets

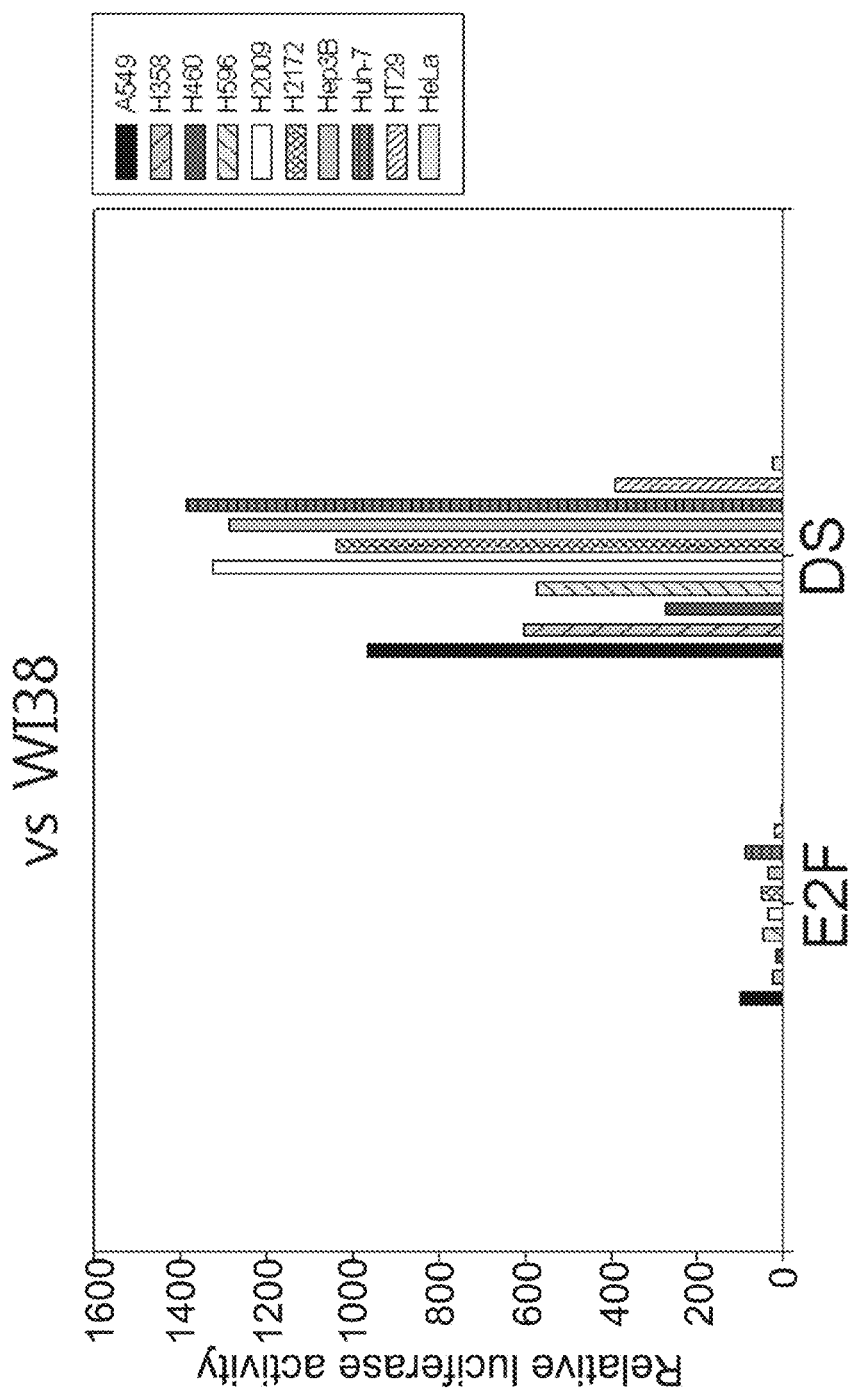

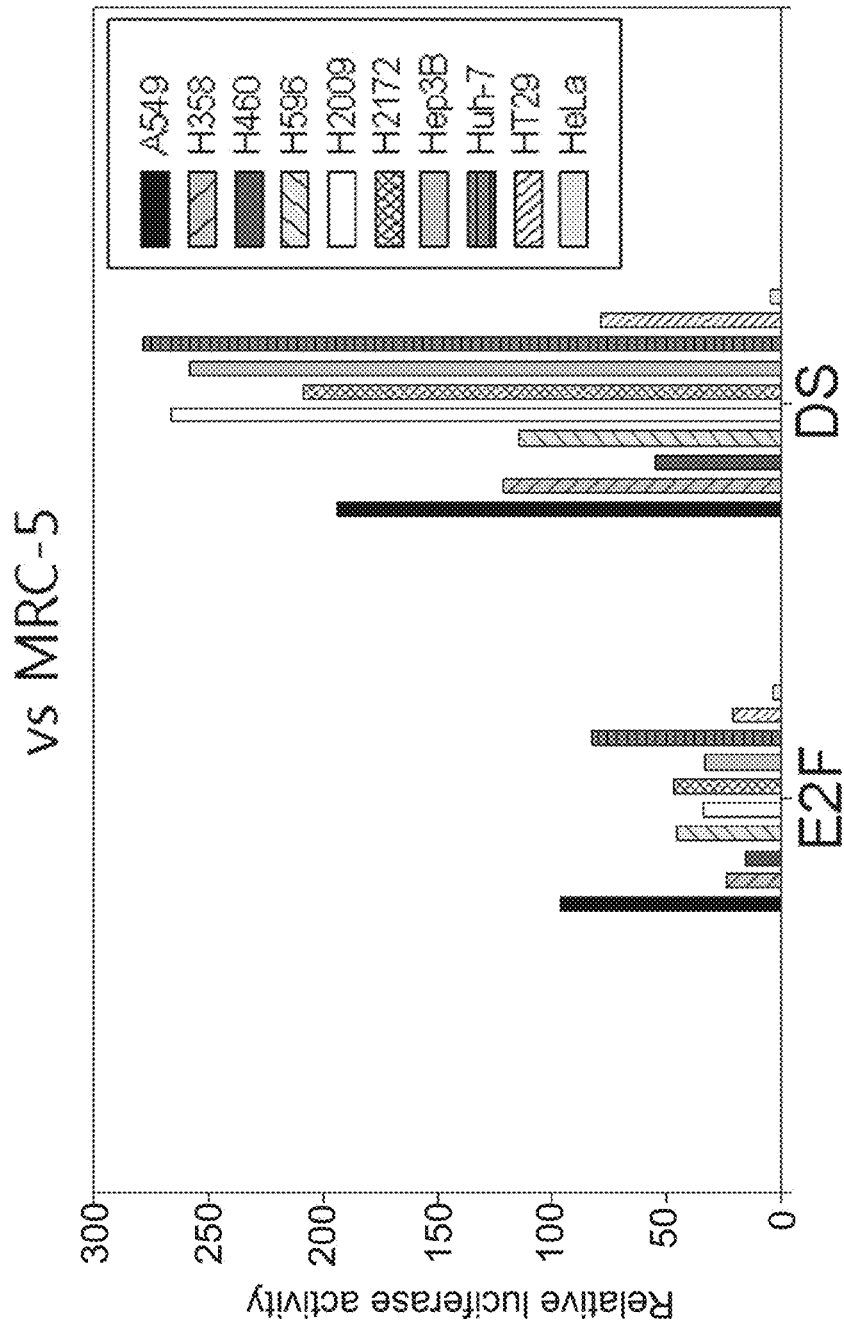

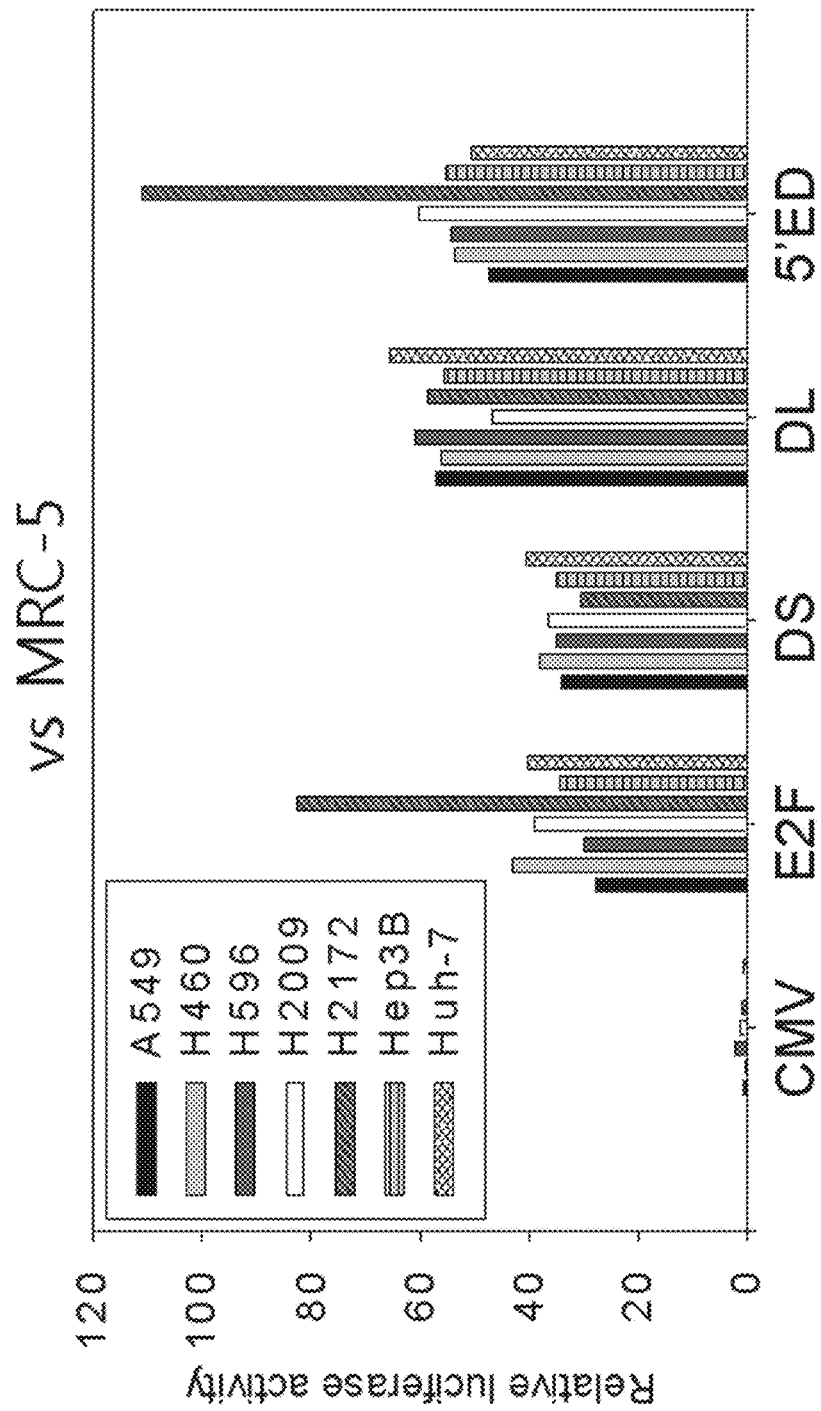

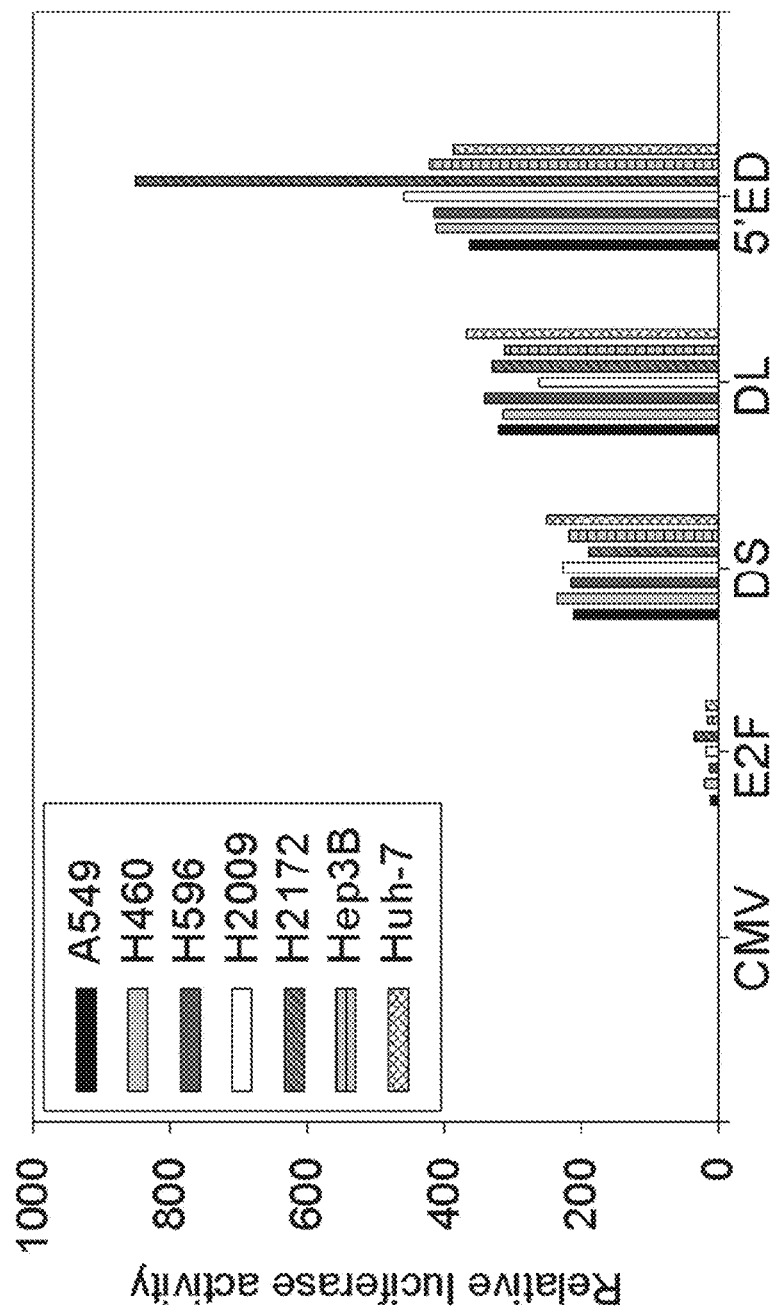

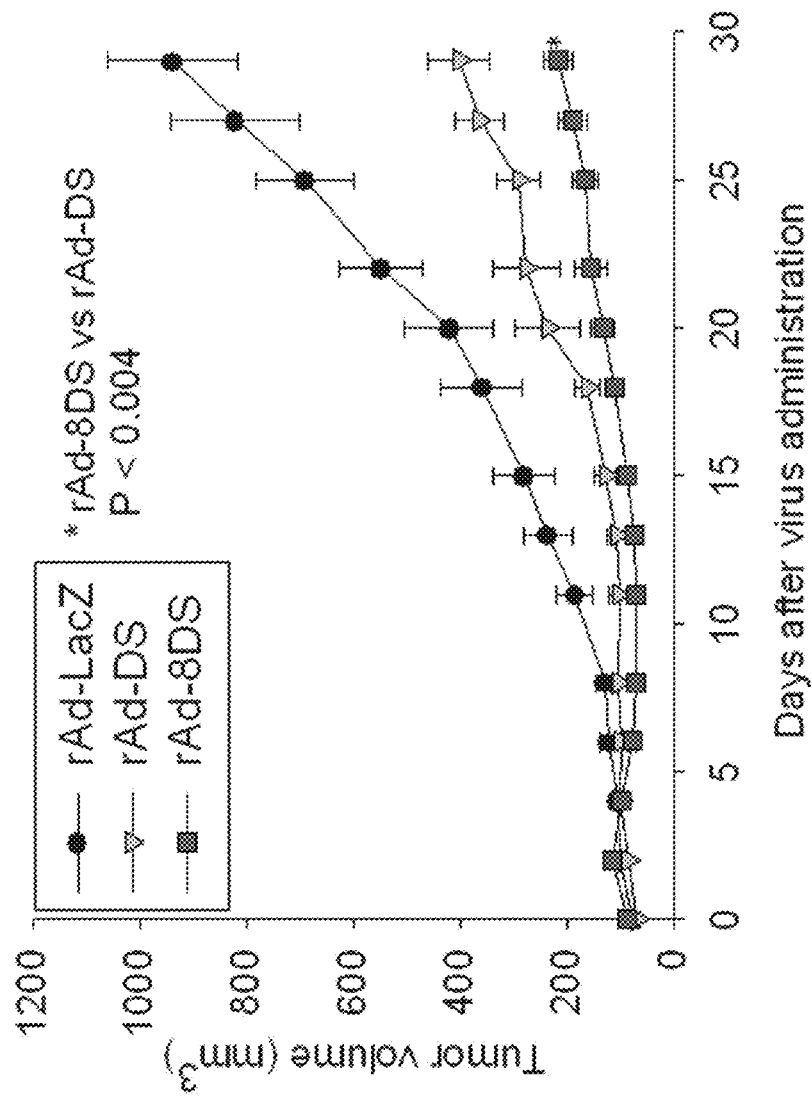

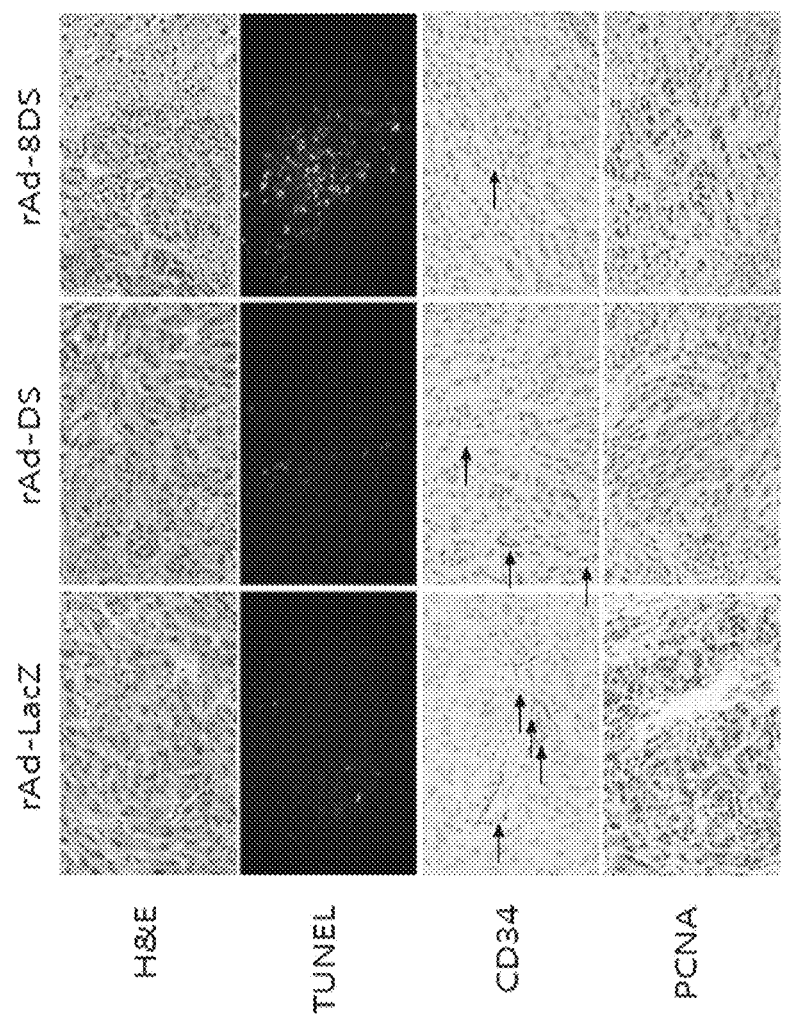

TUMOR SPECIFIC PROMOTER AND ONCOLYTIC VIRUS VECTOR COMPRISING THE SAME

CROSS REFERENCE TO RELATED APPLICATIONS

This application is a National Stage of International Application No. PCT/KR2010/002608 filed Apr. 26, 2010, the content of which is incorporated herein by reference in its entirety.

FIELD OF THE INVENTION

The present invention relates to tumor-specific promoters and oncolytic virus vectors comprising the same.

BACKGROUND OF THE INVENTION

An oncolytic virus is a type of conditionally replication-competent viruses, which selectively replicates in tumor cells to kill them. During the period of the 1950s to 1970s, viral oncolytic effects were demonstrated through studies using adenoviruses and mumps viruses, but eventually failed to draw attention for decades due to its transient efficacy and toxic side effects. However, there was a significant advance in research on an oncolytic virus in the 1990s, since the development of some viruses having improved safety than previous viruses such as thymidine kinase (TK)-deficient mutant of Herpes simplex virus-1 (HSV-1) and an adenovirus mutant, dl1520 (ONYX-015) replicating selectively in p53-defective tumor cells (Jagus R, et al., Int. J. Biochem. Cell. Biol., (1999) 31:123-138; Bischoff J R, et al., Science, (1996) 274(5286):373-376). Until now, about 80 oncolytic viruses have been developed and expected to be promising tools for anticancer therapy.

There have been several approaches in order to enhance the selective replication of viruses in tumor cells and to maximize their oncolytic effects.

The first one is to use a wild-type virus such as Newcastle Disease Virus (NDV) or reovirus which can replicate in tumor cells intactly. These viruses are generally called RNA viruses since they selectively replicate in tumor cells where RNA-activated protein kinase R (PKR)/interferon is deficient.

The second is to enhance the affinity between viruses and tumor cells by bio-engineering. Recently, protein and genetic engineering allow to add a high affinitive ligand, receptor, or antibody to viruses and to give a capsid protein such as fiber high tropism for tumor cells by adding a tumor cell-affinitive ligand thereto.

The third is to introduce modification or deletion into a viral gene to inhibit viral replication and toxicity in normal cells. E1A, one of the adenovirus primary proteins, usually binds to retinoblastoma protein (pRb) in infected cells. The failure of the binding between pRb and E1A by genetic modification results in releasing pRb. In normal cells, the free pRb preferentially binds to E2F-1 which leads to decrease E2F-1 transcriptional activity on viral replication. However, in tumor cells, since pRb gene usually has the mutation and does not bind to E2F regardless of E1A modifications, E2F freely activates transcription for viral replication and cytolysis in spite of viral infection. Another mutant adenovirus, E1B55K gene-deficient adenovirus, is also known to have reduced replication and toxicity in normal cells since it does not have E1B55K gene which inhibit the function of p53 as a tumor suppressor.

The fourth is to edit a viral vector by insertion of foreign genes or deletion of viral genes for enhancing the oncolytic effect. Adenoviral gene E1B19K is known to share homology with Bcl-2 inhibiting cell death, and it was reported that deletion of E1B19K promotes apoptosis of infected cells and enhances the antitumor activity. Further, there has also been an approach for maximizing the antitumor activity by introducing the genes encoding a cytolytic or anti-angiogenic factor such as G-CSF or IL-12 into adenovirus vector.

Finally, the fifth is to utilize a tumor-specific promoter which enables a gene essential for viral replication, e.g., E1A, to be expressed only in tumor cells. Until now, there have been developed several tumor-specific promoters derived from tumor marker genes such as carcinoembryonic antigen (CEA), α-fetoprotein, prostate-specific antigen (PSA), and telomerase (TERT).

However, according to recent studies, it has been reported that the mechanisms of tumorigenesis and metastasis are very diverse and the moiety of tumor cells frequently deviates from these mechanisms. In light of the fact that it is difficult to restrict oncolytic viruses into tumor cells and to increase the oncolytic effect by a single above-mentioned method, it is needed to maximize the therapeutic effect by combining at least one of the methods mentioned above.

Wnt is one of the representative oncogenic factors, which is a vertebrate homologue to the Drosophila segment polarity gene, wingless. Wnt 1 (wingless/int-1) was first identified in mouse mammary tumors induced by MMTV (mouse mammary tumor virus). Likewise, the increased expressions of Wnt2 and Wnt5 were reported in prostate, colon and mammary tumors. In particular, abnormal regulation of Wnt expression in colorectal tumorigenesis is well investigated. Constitutive activation of Wnt has been found in about more than 90% of colorectal cancer which gives rise to the accumulation of β-catenin in nucleus, and the nuclear β-catenin binds to transcription factor TCF to activate the transcription of Wnt target genes. Examples of the Wnt target genes include cell proliferation-involved c-Myc and Cyclin D1, anti-apoptotic factors COX-2 and PPARδ, tumor cell invasion-involved MMPs, growth factors c-met, VEGF and BMP-4. The constitutive activation of Wnt signaling pathway in colorectal cancer is mostly induced by phosphorylation of β-catenin, or the mutation of APC, Axin, or GSK3β, each of which plays an important part in the ubiquitin-related degradation of β-catenin. Recent evidences also suggest that β-catenin participates in mRNA splicing and stabilization by direct binding to pre-mRNA.

Among transcription factor E2F family, E2F-1 was first identified as an E1A-transactivation factor which binds to adenoviral E2A. E2F target genes contain the E2F binding motif of TTT(C/G)CGCG in their promoter regions, and can simultaneously regulate two contradictory phenomena, i.e. cell proliferation and apoptosis. Among currently known E2F target genes, genes encoding cell cycle regulatory factors such as Cyclin E, Cyclin A, Cyclin D, cdc2, and cdc25A; and genes encoding enzymes involved in DNA synthesis such as DHFR (dihydrofolate reductase), DNA polymerase α, and thymidine kinase (TK) are known to be associated with cell proliferation, while genes such as Apaf1 (apoptosis protease-activating factor 1), p'73, and ARF are known to be associated with apoptosis. E2F family binds to pRb called as pocket protein or pRb-related proteins, p107 and p130. Among six members of E2F family currently known, E2F-1, E2F-2, and E2F-3 expressed specifically in the G1/S phase bind with pRb to act as transcriptional activators. In contrast, E2F-4 and E2F-5 bind with p107 and p130 to inhibit the transactivation of E2F target genes. Finally, E2F-6, which lacks both the transactivation domain and the pocket protein-binding domain unlike other E2Fs, is known to inhibit the transactivation of E2F target genes. E2F-1 is generally activated for the transcription of target genes by release from the binding with pRb in case that: 1) pRb is phosphorylated by Cyclin D4/Cdk4 which is activated in G1/S phase; 2) E1A expressed in infected cells with adenovirus competitively binds to pRb; and 3) E2F binding site of pRb is mutated in tumor cells, etc. The activated E2F-1 may facilitate cell proliferation by promoting G1/S transition phase, or induce apoptosis by the transactivation of ARF to inhibit p53 suppressor MDM2.

As described above, the genetic mutation in WNT/β-catenin or malfunction of the E2F/pRb signal transduction is found so frequently in tumor cells, which causes the nuclear accumulation of β-catenin-TCF complex or E2F. Further, the cross-linking between WNT/β-catenin and E2F/pRb signal pathway has been examined via Axin2, Siah1, etc., which may be taken as an excellent tumor marker.

DNMT1 (DNA-methyltransferase 1) is an enzyme that adds methyl groups to DNA, which involves in the methylation of the CpG sites in the transcriptional regulatory region along with HDAC (histone deacetylase). The hypermethylated gene binds with a histone protein to form a tight complex of DNA and protein (heterochromatin), resulting in suppression of DNA transcription.

The present inventors have endeavored to identify a novel tumor-specific promoter in the upstream region of DNMT1 and to construct an adenovirus vector comprising the promoter, which has led the finding that the recombinant adenovirus produced from the vector has a high oncolytic activity.

SUMMARY OF THE INVENTION

Therefore, it is an object of the present invention to provide a novel tumor-specific promoter.

It is another object of the present invention to provide a virus vector comprising the promoter.

It is still another object of the present invention to provide a pharmaceutical composition for treating a cancer comprising the virus vector.

In accordance with one aspect of the present invention, there is provided a tumor-specific promoter having the nucleotide sequence of SEQ ID NO: 8 or 10.

In accordance with another aspect of the present invention, there is provided a viral expression vector which is characterized in regulating a virus genomic gene by the tumor-specific promoter.

In accordance with a still another aspect of the present invention, there is provided a pharmaceutical composition for treating a cancer, comprising the viral expression vector and a pharmaceutically acceptable carrier.

BRIEF DESCRIPTION OF THE DRAWINGS

The above and other objects and features of the present invention will become apparent from the following description of the invention, when taken in conjunction with the accompanying drawings, which respectively show:

FIGS. 2B to 2D: tumor selectivities of tumor-specific promoters, which are represented by the relative luciferase activities in tumor cell lines versus those in normal cell lines (WI38, MRC-5 and SAEC);

FIGS. 4B and 4C: tumor selectivities of promoters CMV, E2F, DS, DL, and 5'ED, which are represented by the relative luciferase activities in various normal cell lines versus those in MRC-5 and WI38, respectively;

FIGS. 15A and 15B: antitumor activities of rAd-8DS and rAd-DS in a lung cancer (H2172) heterotropic transplantation model, in which (A) and (B) exhibit the tumor size and the survival rate of mice, respectively;

FIG. 18C: immunohistochemical result obtained when administering rAd-8DS and rAd-DS to a melanoma (A373SM) orthotropic transplantation mouse model;

DETAILED DESCRIPTION OF THE INVENTION

Figure 1A:
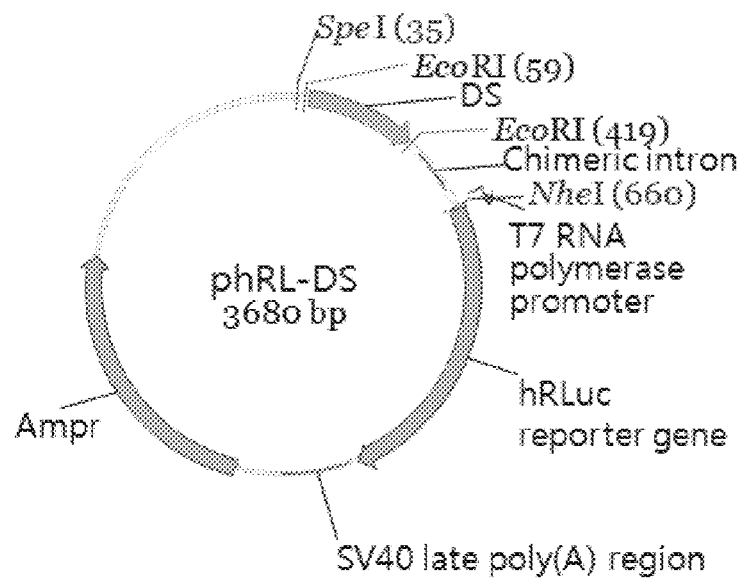
FIGS. 1A and 1B: cleavage maps of the luciferase expression vectors comprising tumor-specific promoters DS and E2F, respectively.

Unless defined otherwise, technical and scientific terms used herein have the same meaning as commonly understood by one of ordinary skill in the art to which the invention belongs. Further, all document mentioned herein are incorporated by reference in their entireties.

The term "adenovirus" as used herein refers to a non-enveloped icosahedral double-stranded DNA virus having about a linear genome of about 36 kb.

The term "tumor-specific promoter" as used herein refers to a promoter which is activated specifically in a tumor cell compared to a normal cell to facilitate a transcription of a gene operably linked to the promoter.

The term "nucleic acid construct" or "nucleic acid cassette" as used herein refers to a nucleotide sequence constructed for insertion to an expression vector.

The term "vector" as used herein refers to a vehicle for gene transfer as that term is understood by those skilled in the art, and includes viruses, plasmids, and the like.

The term "operably linked" used herein refers to the arrangement of various nucleic acid molecule elements relative to each other such that the elements are functionally connected and are able to interact with each other.

The present invention is described in detail hereinafter.

The present invention provides a tumor-specific promoter having the nucleotide sequence of SEQ ID NO: 8 or 10.

The present inventors tried to investigate tumor-specific promoters from the upstream region of DNMT-1 (DNA methylransferase-1) gene. As a result, a 343 bp-long promoter having the nucleotide sequence of SEQ ID NO: 8 was selected and designated "DS promoter," and a 1108 bp-long promoter having the nucleotide sequence of SEQ ID NO: 10, which contains the DS promoter, was further selected and designated "DL promoter." Further, a 692 bp-long promoter having the nucleotide sequence of SEQ ID NO: 12 was constructed by fusing the DS promoter with a 5'E2F fragment where 5' region of E2F promoter is deleted, and the promoter was designated "5'ED promoter." The inventive promoters show significant tumor selectivities in comparison with a previously established tumor-specific promoter E2F (see FIGS. 2 and 4).

The tumor-specific promoter having the nucleotide sequence of SEQ ID NO: 8 or 10 may further comprise an additional nucleotide sequence inserted into or linked to the nucleotide sequence of SEQ ID NO: 8 or 10, as long as the resultant promoter exhibits the tumor-specific promoter activity. The additional nucleotide is any nucleotide sequence known to those skilled in the art, and an exogenous promoter is preferred. Examples of the exogenous promoters include ubiquitous promoter (CMV, SV40, TK, β-actin, elF4A1, GAPDH, EF1, hsp70 and ubiquitin B), tissue-specific promoter (albumin, α1-antitrypsin protease, FVII, B29, CD14, CD43, CD45, CD68, elastase-1, endoglin, fibronectin, flt-1, GFAP and ICAM-2) and tumor-specific promoter (E2F1, TERT, PSA, AFP, CEA, survivin, COX-2, CXCR4 and MUC1), but not limited thereto.

The present invention provides a tumor-specific promoter comprising the fragment of the nucleotide sequence of SEQ ID NO: 8 or 10, the fragment exhibiting the tumor-specific promoter activity. The preferable fragment may be one which comprises the nucleotide sequence of SEQ ID NO: 8 and does not exceed the nucleotide sequence of SEQ ID NO: 10.

The tumor-specific promoter comprising the fragment of the nucleotide sequence of SEQ ID NO: 8 or 10 may further comprise an additional nucleotide sequence inserted into or linked to the fragment of the nucleotide sequence of SEQ ID NO: 8 or 10, as long as the resultant promoter exhibits the tumor-specific promoter activity. The additional nucleotide is any nucleotide sequence known to those skilled in the art, and an exogenous promoter is preferred. Examples of the exogenous promoters include ubiquitous promoter (CMV, SV40, TK, β-actin, elF4A1, GAPDH, EF1, hsp70 and ubiquitin B), tissue-specific promoter (albumin, α1-antitrypsin protease, FVII, B29, CD14, CD43, CD45, CD68, elastase-1, endoglin, fibronectin, flt-1, GFAP and ICAM-2) and tumor-specific promoter (E2F1, TERT, PSA, AFP, CEA, survivin, COX-2, CXCR4 and MUC1), but not limited thereto.

Further, the present invention provides a nucleic acid construct or a nucleic acid cassette, comprising the tumor-specific promoter. The nucleic acid construct of the present invention may further comprise an exogenous gene operably linked to the tumor-specific promoter. The exogenous gene may preferably be a gene essential for virus replication known to those skilled in the art, more preferably, an adenoviral gene selected from the group consisting of E1A, E1B, E2A, E2B, E3, E4, L1, L2, L3, L4, and L5. Furthermore, the present invention provides an expression vector comprising the nucleic acid construct.

Moreover, the present invention provides an expression vector which expresses the genomic gene of a virus under the regulation of the tumor-specific promoter according to the present invention. The virus may preferably be selected from the group consisting of adenovirus, adeno-associated virus, retrovirus, lentivirus, herpes simplex virus, reovirus, etc., more preferably, an adenovirus, and most preferably an adenovirus derived from primates. Adenoviruses infect both non-dividing and dividing cells unlike retroviruses and replicate as episomal elements in the nucleus without integrating with host genome, thereby not disrupting host genome. Adenoviruses are also useful for gene therapy due to high efficacy, long and safe storage, and low restriction in inserting an exogenous gene.

Meanwhile, the viral genomic gene may preferably be a gene essential for viral replication, more preferably, a gene essential for adenoviral replication and synthesis. Once the adenovirus infects the host cell, the early genes including E1A gene essential for replication (e.g., E1B, E2A, E2B, E3, and E4) are transcribed and 5 to 7 hours after infection the late genes (e.g., L1, L2, L3, L4 and L5) are transcribed to induce the synthesis of capsid protein together with the inhibition of DNA synthesis in the host cell. Accordingly, the genomic gene of an adenovirus may preferably be selected from the group consisting of E1A, E1B, E2A, E2B, E3, E4, L1, L2, L3, L4, and L5.

Specifically, the viral expression vector of the present invention is an expression vector comprising a viral genome, the vector being characterized in regulating the genomic gene of a virus with the tumor-specific promoter. That is, in the expression vector, the genomic gene of a virus may operably linked to the tumor-specific promoter or an endogenous promoter in viral genome may be replaced with the tumor-specific promoter of the present invention.

The viral expression vector of the present invention may comprise an exogenous nucleotide sequence. The exogenous nucleotide sequence may be selected from the group consisting of tumor suppressor genes, cytotoxic genes, cytostatic genes, cytokines, suicide genes, and antigen-encoding genes. Examples of tumor suppressor genes include WT1, p53, p16, Rb, BRCA1, and LK8.

The tumor suppressor gene LK8 is known to directly target the vascular endothelial cells to induce the cytotoxicity and inhibit the transit of endothelial cells (Kim J S et al., J. Biol. Chem., (2003) 278:29000). In particular, it was reported that hepatocellular carcinoma growth in mice was suppressed by administering an adenoviral vector containing LK8 gene (Lee K et al., Hepatology., (2006) 43:1063), and it is therefore anticipated that the adenoviral oncolytic effect would increase by the introduction of LK8. The LK8 gene may be obtained by any of methods known in the art, e.g., may be obtained from a plasmid, pAAV-CMV_LK8_UN disclosed in WO2009/102085.

The suicide genes, involved in the process of programmed cell death or apoptosis, may be any one selected from the group consisting of herpes simplex virus thymidine kinase, cytosine deaminase, purine nucleoside phosphorylase, β-lactamase, carboxypeptidase G2, cytochrome, p450-2B1, nitroreductase and β-glucuronidase.

Further, in the viral expression vector of the present invention, a part of the genomic genes of a virus included in the vector may be replaced with other gene. For instance, E1A gene in adenoviral genome may be replaced with a mutant E1A gene having the nucleotide sequence of SEQ ID NO: (17), or E1B gene in adenoviral genome may be replaced with E1B55K where the 19 KDa region of E1B is deleted. The mutant E1A gene is a gene in which Glu in CR1 site, known as pRb binding site, is replaced with Gly and seven (7) amino acids (DLTCHEA) present in CR2 coding region is replaced with 7 Glycines, as used in a vector (Ad-E1mt7-ΔE1B19) suggested by Kim et al. (Kim J S et al., Human Gene Ther., (2007) 18:773). In addition, the E1B-deficient gene may be the E1B55K gene in which the 19 kDa region of E1B is deleted. In an alternative embodiment of the present invention, a gene encoding a capsid protein or fiber protein may be replaced with that of a different serotype, preferably a gene encoding a fiber protein of adenovirus serotype 35 (See FIGS. 19 to 21).

Figure 9A:
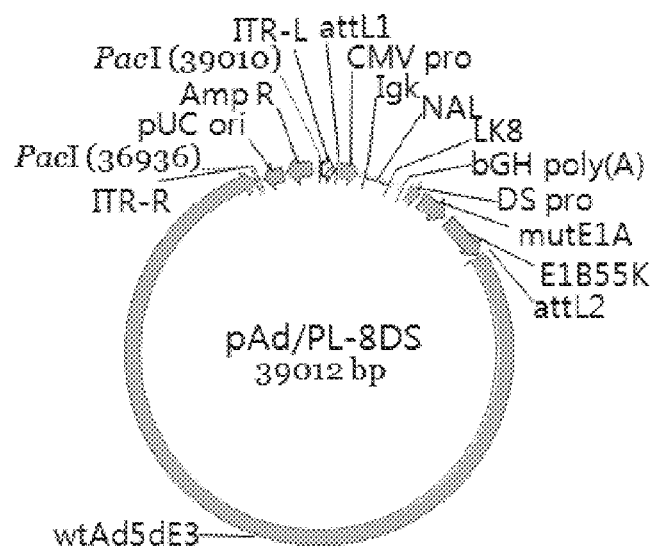
FIGS. 9A to 9D: cleavage maps of adenoviral vectors comprising the tumor-specific promoter or LK8 gene.
Figure 9B:
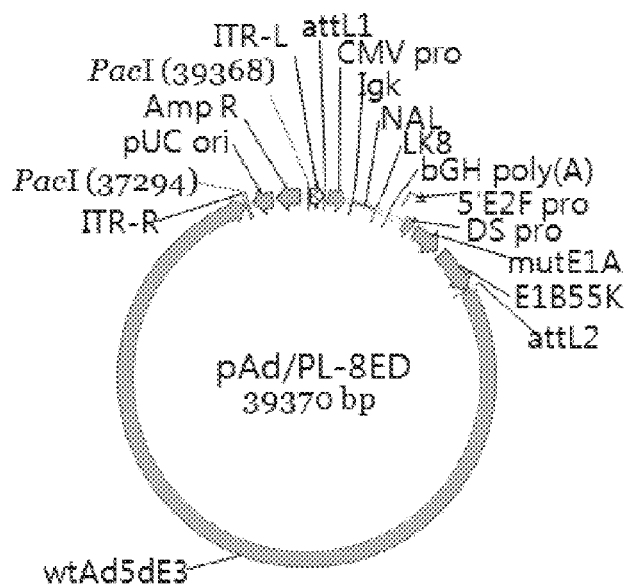
Figure 9C:
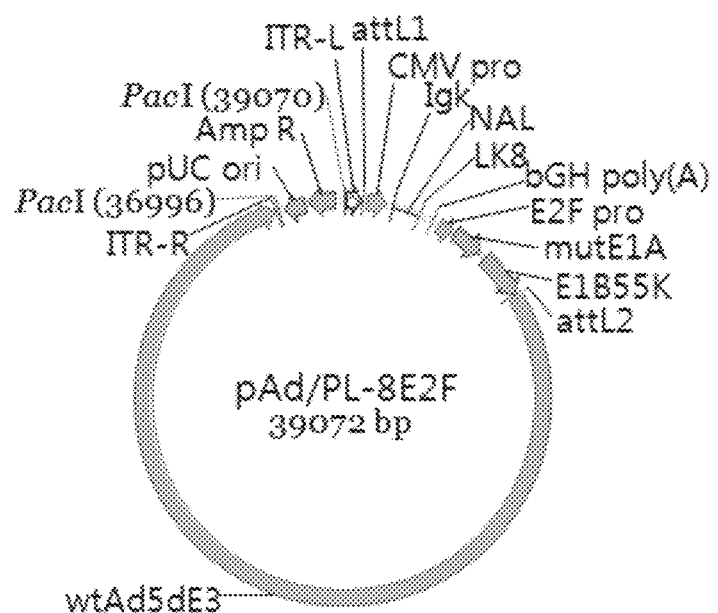
Figure 9D:
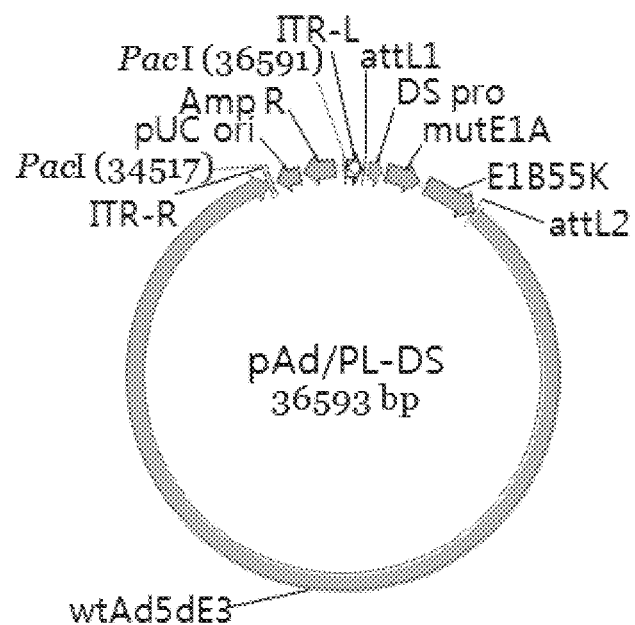

Exemplary viral expression vector comprising the tumor-specific promoter of the present invention includes, but not limited thereto, pAd/PL-8DS vector represented by FIG. 9A, pAd/PL-8ED vector represented by FIG. 9B, and pAd/Pl-DS vector represented by FIG. 9D, and it would be appreciated that various viral vectors can be constructed using a number of previously known backbone plasmids by those skilled in the art.

In the present invention, there is also provided a pharmaceutical composition comprising the viral expression vector and a pharmaceutically acceptable excipient or carrier. The composition of the present invention is useful for gene therapy, preferably for cancer treatment.

The pharmaceutically acceptable excipient or carrier contained in the pharmaceutical composition of the present invention may include, but not limited to, saline solutions, suitable buffers, preservatives and stabilizers. Examples of suitable excipients or carriers are water, salt water, alcohol, lipid, wax, buffer solution, solid carrier such as mannitol, lactose, starches, magnesium stearate, sodium saccharin, talc, cellulose, glucose, sucrose, and magnesium carbonate, or biodegradable microsphere (e.g., polylactate polyglycolate).

The composition of the present invention may be provided in the form of single dose or multi-dose container such as sealed ampule or vial. Preferably, such container may be sealed so as to conserve aseptic condition of pharmaceutical formulations before using. In general, the formulation may be preserved as suspension, fluid, and emulsion in oil or aqueous vehicle. Further, the pharmaceutical formulation may be preserved under freeze drying conditions.

The pharmaceutical compositions of the present invention may be administered with site-specific injection or intravenous injection. Site-specific injection includes, for example, intraperitoneal injection, intrapleural injection, intrathecal injection, intraarterial injection, intratumoral injection or local application. The preferred method is intravenous injection.

It should be understood that the suitable amount of the active ingredient actually administered ought to be determined in light of various relevant factors including the condition to be treated, the age and weight of the individual patient, food, administration time, excretion rate, the severity of the patient's symptom and reaction susceptibility; and, therefore, the above dose should not be intended to limit the scope of the invention in any way. Generally, the adenoviral vector contained in the pharmaceutical composition may be administered in an appropriate physiologically acceptable carrier at a dose of about $10^4$ to about $10^{14}$ vp/mL. The multiplicity of infection may be generally in the range of 0.001 to 100. If administered as a polynucleotide construct, about 0.01 to 1000 µg/kg of an adenoviral vector can be administered. The adenoviral vector may be administered one or more time, depending upon the intended use and the immune response potential of the host, and may also be administered as multiple, simultaneous injections. If an immune response is undesirable, the immune response may be diminished by employing a variety of immunosuppressants, or by employing a technique such as an immunoadsorption procedure (e.g., immunoapheresis) that removes adenovirus antibody from the blood, so as to permit repetitive administration, without a strong immune response.

The composition of the present invention may be used as the single therapy. But it may be combined with other anti-tumor protocols, such as conventional chemotherapy or radiation therapy for treating cancer. The chemotherapy drug which can be used with composition of the present invention encompasses paclitaxel, cisplatin, carboplatin, procarbazine, mechlorethamine, cyclophosphamide, ifosfamide, melphalan, chlorambucil, bisulfan, nitrosourea, dactinomycin, daunorubicin, doxorubicin, bleomycin, plicomycin, mitomycin, etoposide, tamoxifen, taxol, transplatinum, 5-fluorouracil, vincristin, vinblastin and methotrexate. The radiation therapy which can be used with the composition of the present invention may be X-ray irradiation and γ-ray irradiation, etc.

The adenovirus produced from the adenoviral vector of the present invention shows high oncolytic effect in tumor cells, while low effect in normal cells from in vitro and in vivo experiments. Thus, the viral vector comprising the tumor-specific promoter of the present invention may be used for treating a cancer.

The following Examples are given for the purpose of illustration only, and are not intended to limit the scope of the invention.

Example 1

Identification of Tumor-Specific Promoters Comprising the Binding Site of a Transcription Factor E2F-1 or TCF-1 and Analysis of their Activities <1-1> Identification of Tumor-Specific Promoters In order to select a tumor-specific promoter, the upstream region ranging from the initiation codon to 2,000 base pairs of hDNMT-1 (Genbank Accession No. NC_000019) was analyzed. Briefly, a transcriptional regulatory element containing TTT(C/G)GCGC sequence known as the binding motif of the transcription factor E2F-1 and (A/T)(A/T)CAAAG sequence known as the binding motif of the transcription factor TCF-1 involved in WNT signaling pathway was searched, and a transcription binding prediction map was prepared using a transcription binding site prediction program TRANSFAC (Heinemeyer T et al., Nucleic Acids Res., (1998) 26:364) and TFSEARCH (http://mbs.cbrc.jp). Based on the map, PCR reaction was carried out using a human genomic DNA (Clontech, CA) as a template, sense and antisense primers of SEQ ID NOs: 1 and 2, respectively, and Ex-Taq polymerase (Takara, Japan). The reaction was conducted under the following conditions: an initial denaturation at 94° C. for 5 min, followed by 30 cycles of denaturation at 94° C. for 30 sec, annealing at 56° C. for 30 sec, and extension at 72° C. for 1 min, followed by a final extension at 72° C. for 1 min. The DNA fragment (DS promoter) amplified by PCR was purified by gel extraction and inserted into pCR2.1-TOPO plasmid vector (Invitrogen, CA) to construct pCR-DS. The insertion of "DS promoter" having the nucleotide sequence of SEQ ID NO: 8 was identified by the cleavage map using restriction enzymes and the nucleotide sequence analysis. The plasmid was digested with EcoRI and the digested fragment was inserted into a luciferase reporter vector phRL-null (Promega, WI) to construct phRL-DS plasmid (FIG. 1A).

Figure 1B:
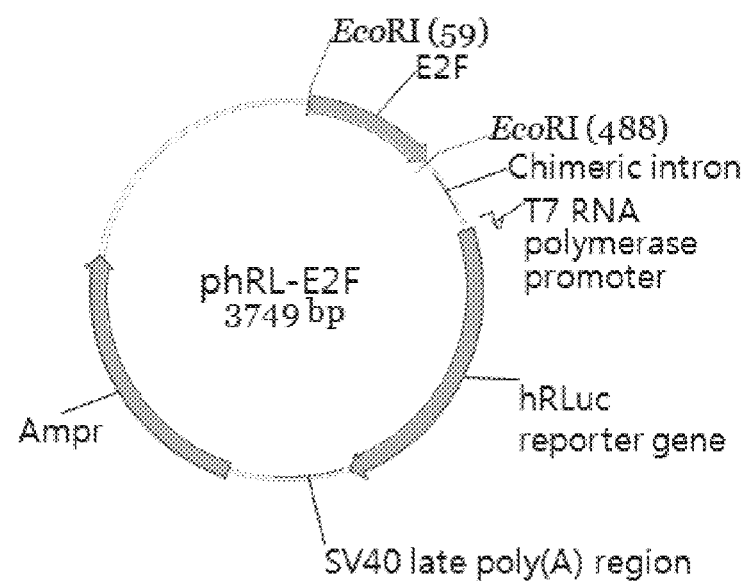

In addition, as a control, E2F promoter previously established was synthesized by repeating the above PCR reaction except for using sense and antisense primers of SEQ ID NOs: 3 and 4, respectively. The fragment amplified by PCR was inserted into pCR2.1-TOPO plasmid vector and the fragment containing the promoter was inserted into phRL-null vector according to the method mentioned above to construct phRL-E2F plasmid containing hE2F-1 promoter of SEQ ID NO: 9 (FIG. 1B).

Meanwhile, luciferase vectors phRL-CMV and phRL-SV40 (Promega, WI) containing conventional promoters CMV and SV40, respectively, were used as controls.

The obtained promoters, nucleotide sequences thereof, and primers used for PCR are shown in Table 1.

TABLE 1

| Promoter | Nucleotide sequence | PCR primer |
|---|---|---|
| DS promoter | SEQ ID NO: 8 | Sense primer (SEQ ID NO: 1); Antisense primer (SEQ ID NO: 2) |
| E2F promoter | SEQ ID NO: 9 | Sense primer (SEQ ID NO: 3); Antisense primer (SEQ ID NO: 4) |

<1-2> Measurement of Luciferase Activity by the Tumor-Specific Promoter

In order to measure the tumor cell specificity of DS promoter obtained in Example 1, luciferase activity was analyzed using normal and tumor cells and the luciferase reporter vector.

As a normal cell line, MRC-5 (lung fibroblast, ATCC CCL-171), WI38 (lung fibroblast, ATCC CCL-75), SAEC (small airway epithelial cell, CAMBREX, U.S.), HMEC (mammary epithelial cell, CAMBREX, U.S.), PrEC (prostate epithelial cell, CAMBREX, U.S.), HRE (human renal epithelial cell, CAMBREX, U.S.) and bMVEC-B (Brain microvascular endothelial cell, CAMBREX, U.S.) were used. As a tumor cell line, A549 (non-small cell lung cancer, ATCC CCL-185), H358 (non-small cell lung cancer, ATCC CRL-5807), H460 (non-small cell lung cancer, ATCC HTB-177), H596 (non-small cell lung cancer, ATCC HTB-178), H2009 (non-small cell lung cancer, ATCC CRL-5911), H2172 (non-small cell lung cancer, ATCC CRL-5930), Hep3B (hepato-cellular carcinoma, ATCC HB-8064), Huh-7 (hepato-cellular carcinoma, KCLB 60104), HeLa (cervical carcinoma, ATCC CCL-2), DU145 (prostate cancer, ATCC HTB-81), C33A (cervical cancer, ATCC HTB-31), Miapaca-2 (pancreatic cancer, ATCC CRL-1420), MDA-MB-231 (breast cancer, ATCC HTB-26), HT29 (colorectal carcinoma, ATCC HTB-38) and U2OS (osteosarcoma, ATCC HTB-96) were used. Each cell was cultured in accordance with the manufacturer's culture method.

Specifically, the normal and tumor cells were cultured in each well of a six-well plate (TPP, Switzerland) with the number of $4 \times 10^5$ cells/well. The cultured cells were co-transfected with 2 μg of each luciferase vector constructed in Example <1-1> and 1 μg of pcDNA-LacZ using a polyethyleneimine transfection reagent (Jet-PEI, Polyplus, France). The transfected cells were cultured at 37° C. for 48 hours, harvested by addition of trypsin-EDTA, and centrifuged at 3,000 rpm for 5 min to separate cells and media. The separated cells were resuspended in 200 μL of a lysis buffer (25 mM Tris-phosphate, pH 7.8, 2 mM DTT (Dithiothreitol), 2 mM 1,2-diaminocyclohexane N,N,N,N'-tetra acetic acid, 10% glycerol, 1% Triton® X-100) followed by freezing and thawing (×2) to lyse the cells. The cell lysates were centrifuged at 10,000 rpm for 5 min. 80 μL of the resultant supernatant was subjected to enzyme-substrate reaction using luciferase assay kit (Renilla Luciferase Assay System, Promega, WI), followed by analyzing luciferase activity using Fluorescence Microplate Reader (Microlumat Plus, EG&G BERTHOLD, Germany). In order to correct transfection efficiency, 25 μL of the supernatant was also subjected to enzyme-substrate reaction using β-galactosidase assay kit (β-Galactosidase Enzyme Assay System, Promega, WI) and the absorbance was then measured using a Spectra Shell Microplate Reader (STL Spectra, Italy) at 450 nm. Further, in order to correct protein concentration in cells, 10 μL of the supernatant was subjected to protein staining using a Bradford dye (BIO-RAD Protein dye, Bio-Rad, CA), followed by measuring the absorbance at 595 nm. The luciferase activity induced by the promoter was shown in FIG. 2A with the relative value based on a galactosidase activity value and protein concentration.

Figure 2A:
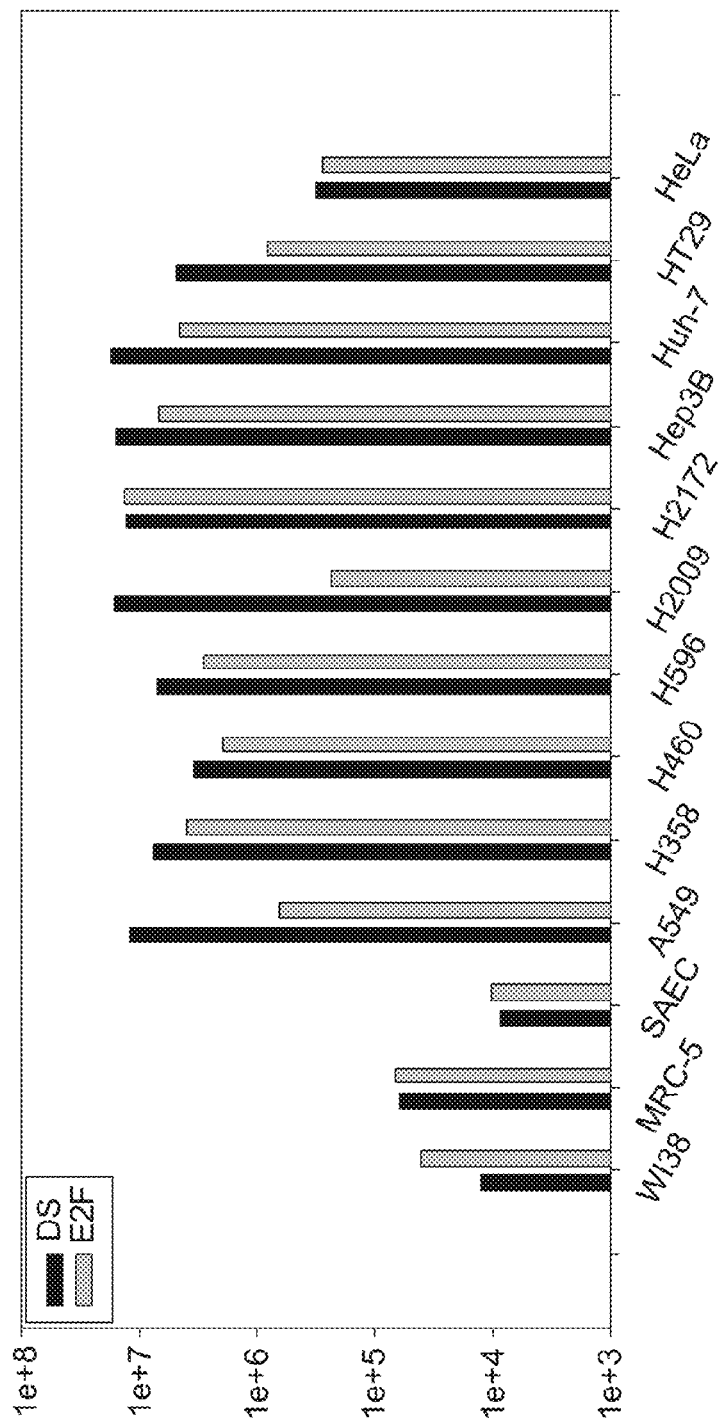
FIG. 2A: relative luciferase activities induced by tumor-specific promoters in normal cell lines (WI38, MRC-5 and SAEC) and tumor cell lines (A549, H358, H460, H596, H2009, H2172, Hep3B, Huh-7, HT29 and Hela)
Figure 2D:
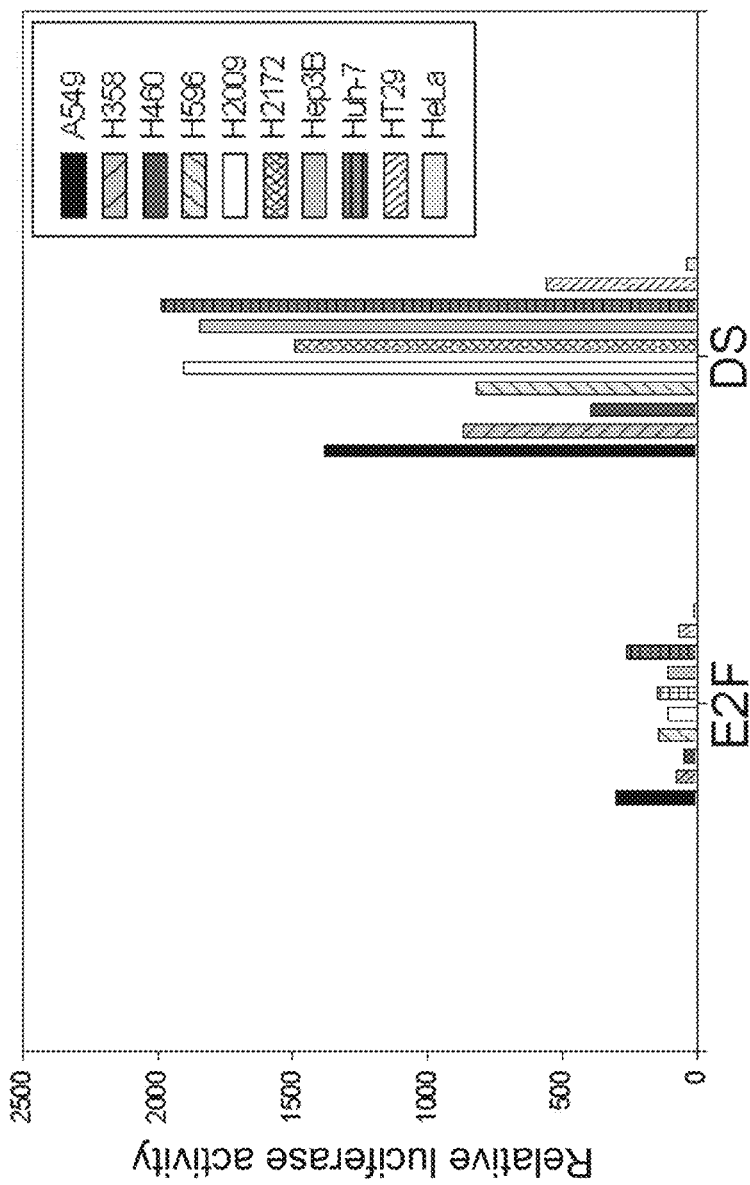

As shown in FIG. 2A, DS promoter induced high luciferase activity in tumor cells than normal cells, and the luciferase activity induced by DS promoter was equivalent or ten-fold higher than that induced by the tumor-specific promoter E2F. In particular, in terms of tumor-specificity of the promoter, which was calculated by dividing the activity values of normal cells (e.g., WI38, MRC-5 and SAEC) by that of tumor cells, DS promoter was 2.5 to 100-fold higher than E2F promoter (FIGS. 2B to 2D).

<1-3> Construction of Modified DS Promoters

In order to investigate the change of a tumor-specific activity depending on modification of DS promoter obtained in Example <1-1>, three modified promoters were constructed: a) DL promoter having the nucleotide sequence of SEQ ID NO: 10, which contains DS promoter; b) 5'E2F promoter having the nucleotide sequence of SEQ ID NO: 11, in which 5' region of E2F promoter is deleted; and c) 5'ED promoter having the nucleotide sequence of SEQ ID NO: 12, in which 5'E2F promoter is fused with DS promoter.

Figure 3A:
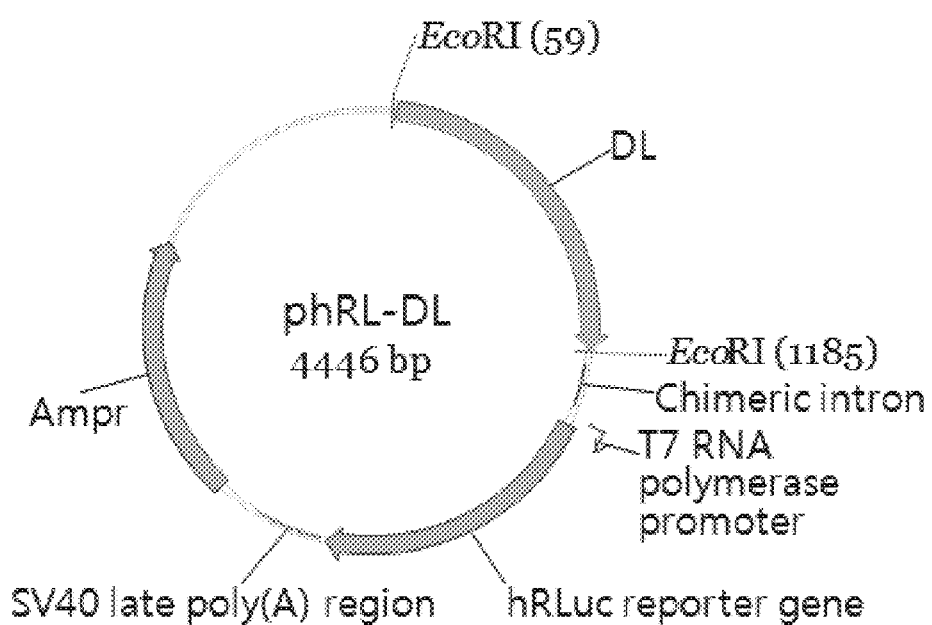
FIGS. 3A to 3C: cleavage maps of luciferase expression vectors comprising the DL promoter as a modified DS promoter, short type of 5'E2F promoter, and 5'ED promoter, respectively.

Specifically, DL promoter having the nucleotide sequence of SEQ ID NO: 10 was obtained by repeating the PCR reaction as described in Example <1-1> except for using sense and antisense primers of SEQ ID NOs: 5 and 2, respectively, and was inserted into pCR2.1-TOPO plasmid vector to construct pCR-DL. The plasmid pCR-DL was digested with EcoRI, and the digested fragment was inserted into phRL-null vector digested with EcoRI to construct a luciferase vector, phRL-DL, which contains DL promoter having the nucleotide sequence of SEQ ID NO: 10 (FIG. 3A).

Figure 3B:
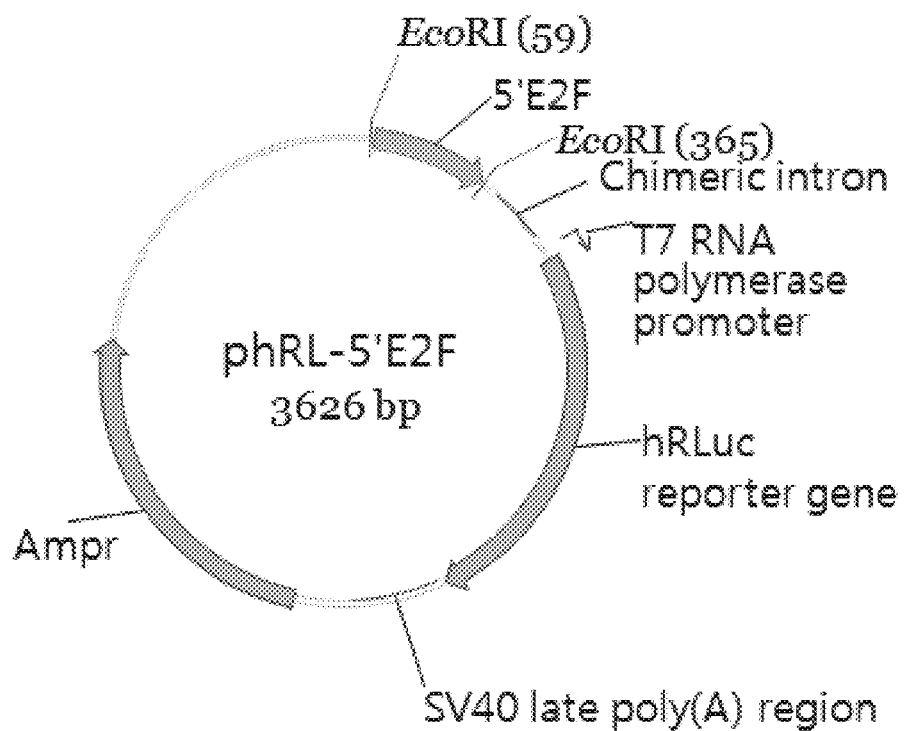
Figure 3C:
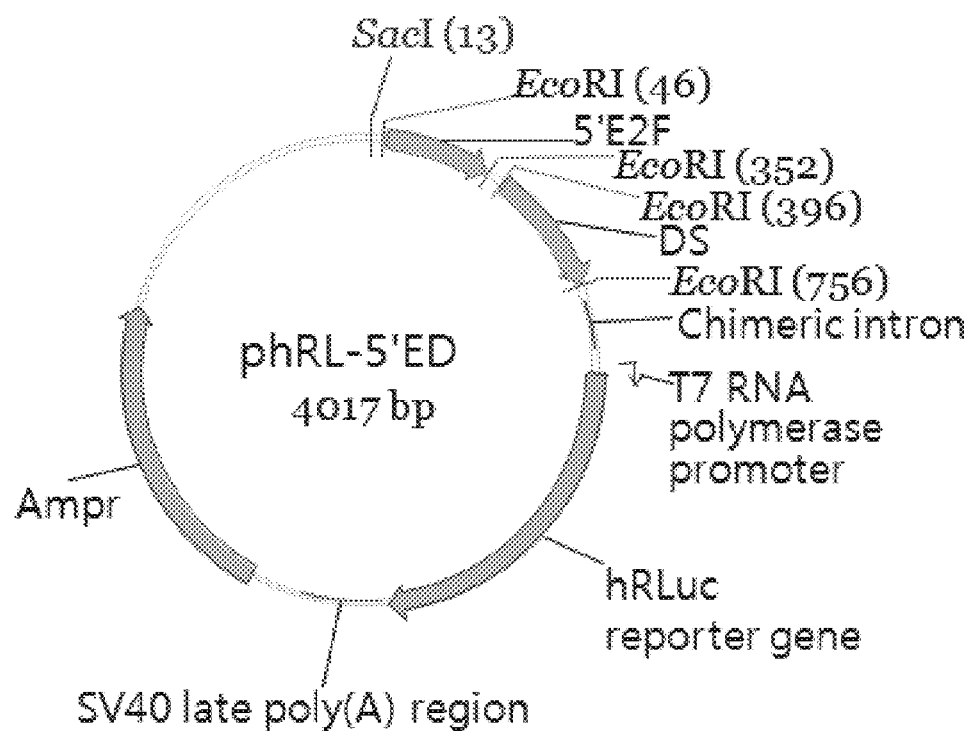

Further, 5'E2F promoter having the nucleotide sequence of SEQ ID NO: 11 was obtained by repeating the RCR reaction as described in Example <1-1> except for using sense and antisense primers of SEQ ID NOs: 6 and 4, respectively, and was inserted into pCR2.1-TOPO plasmid vector to construct pCR-5'E2F. The plasmid pCR-5'E2F was digested with EcoRI, and the digested fragment was inserted into phRL-null vector digested with EcoRI to construct a luciferase vector, phRL-5'E2F, which contains 5'E2F promoter having the nucleotide sequence of SEQ ID NO: 11 (FIG. 3B).

Furthermore, the pCR-5'E2F plasmid was digested with SacI and XhoI, and the digested fragment was inserted into SacI/SalI site of the phRL-DS plasmid described in Example <1-1> to construct phRL-5'ED plasmid which contains 5'ED promoter having the nucleotide sequence of SEQ ID NO: 12.

<1-4> Measurement of Luciferase Activity of the Modified DS Promoter

Figure 4A:
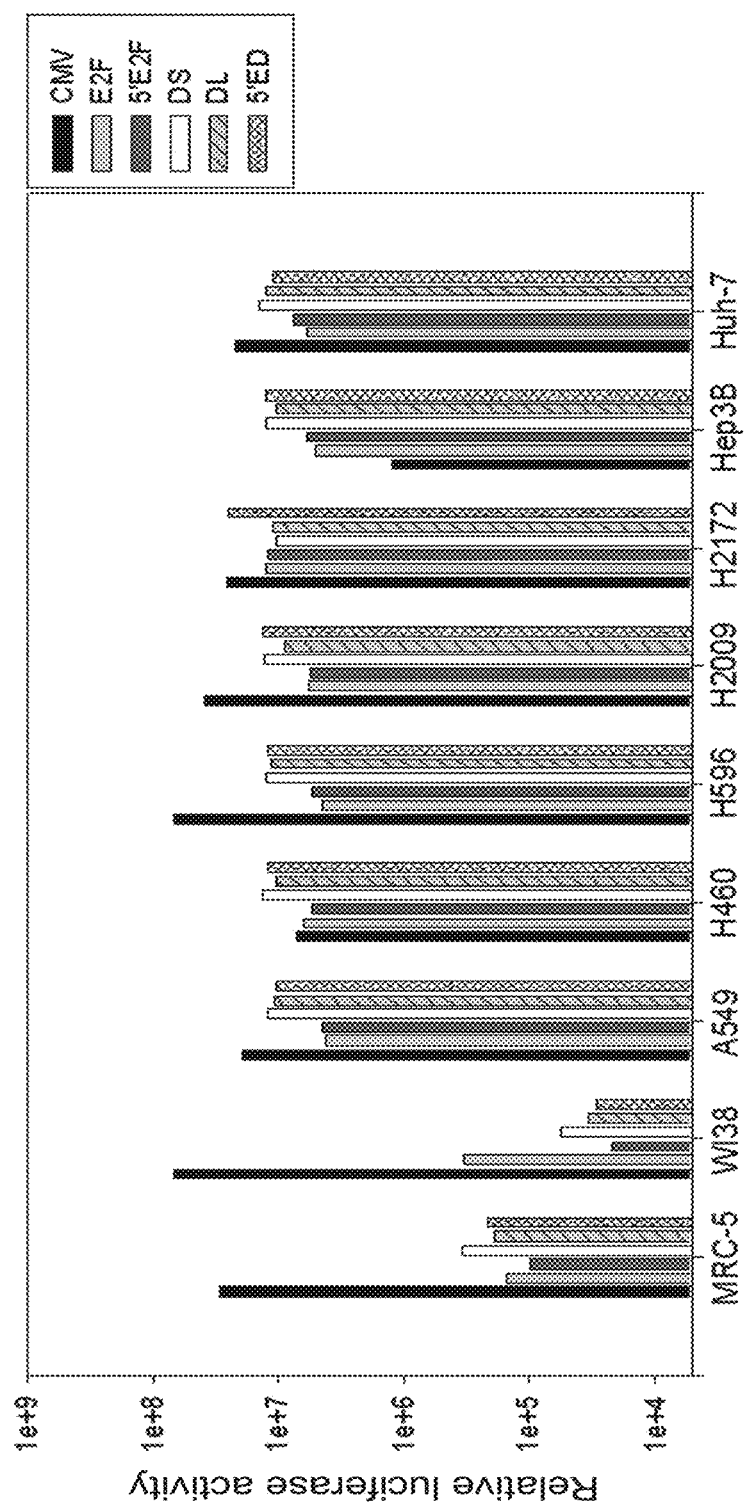
FIG. 4A: relative luciferase activities induced by promoters CMV, E2F, 5'E2F, DS, DL, and 5'ED, respectively.

The plasmids, phRL-DS, phRL-DL, phRL-5'ED, phRL-E2F, phRL-5'E2F and phRL-CMV were transfected into each cell line, respectively, as described in Example <1-2>. The luciferase activities induced by the promoters are shown in FIG. 4A.

As a result, CMV promoter used as a negative control to the tumor-specific promoter showed no luciferase activity in tumor cells, which means CMV promoter is not tumor-specific. Meanwhile, the tumor-specific promoters including DS promoter showed high luciferase activity in tumor cells in comparison with normal cells. The modified DS promoters such as DL and 5'ED promoters showed no increased activity compared to DS promoter in tumor cells. However, DL and 5'ED promoters exhibited 50-100% improved tumor selectivity than DS promoter in normal cells such as MRC-5 and WI-38, and particularly, 20 times or more superior tumor selectivity to E2F promoter in WI-38 (FIGS. 4B and 4C).

<1-5> Verification on Mechanism of the Tumor-Specific Promoter Activity

Figure 5A:
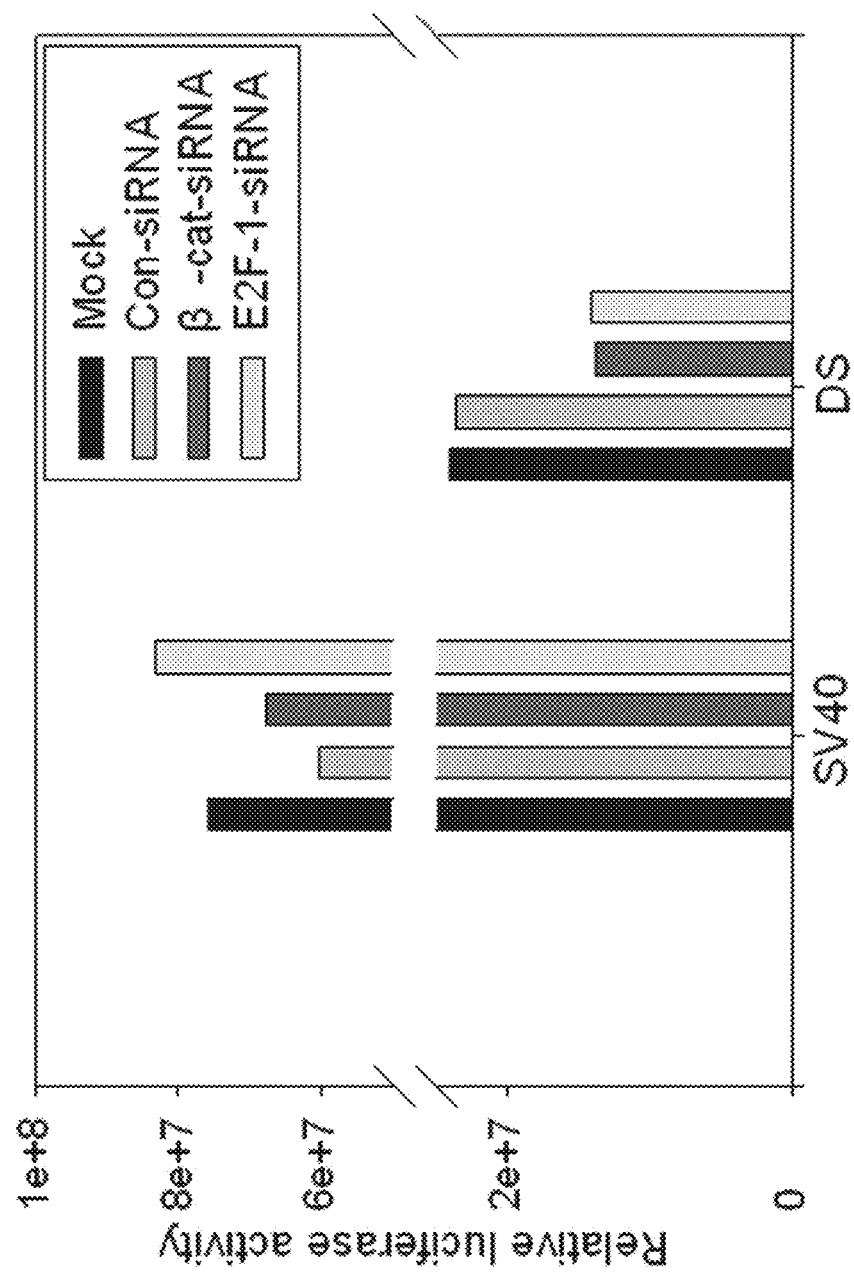
FIG. 5A: relative luciferase activities induced by DS and SV40 promoters, after treatment of mock, control siRNA, β-catenin siRNA and E2F-1 siRNA, respectively.
Figure 5B:
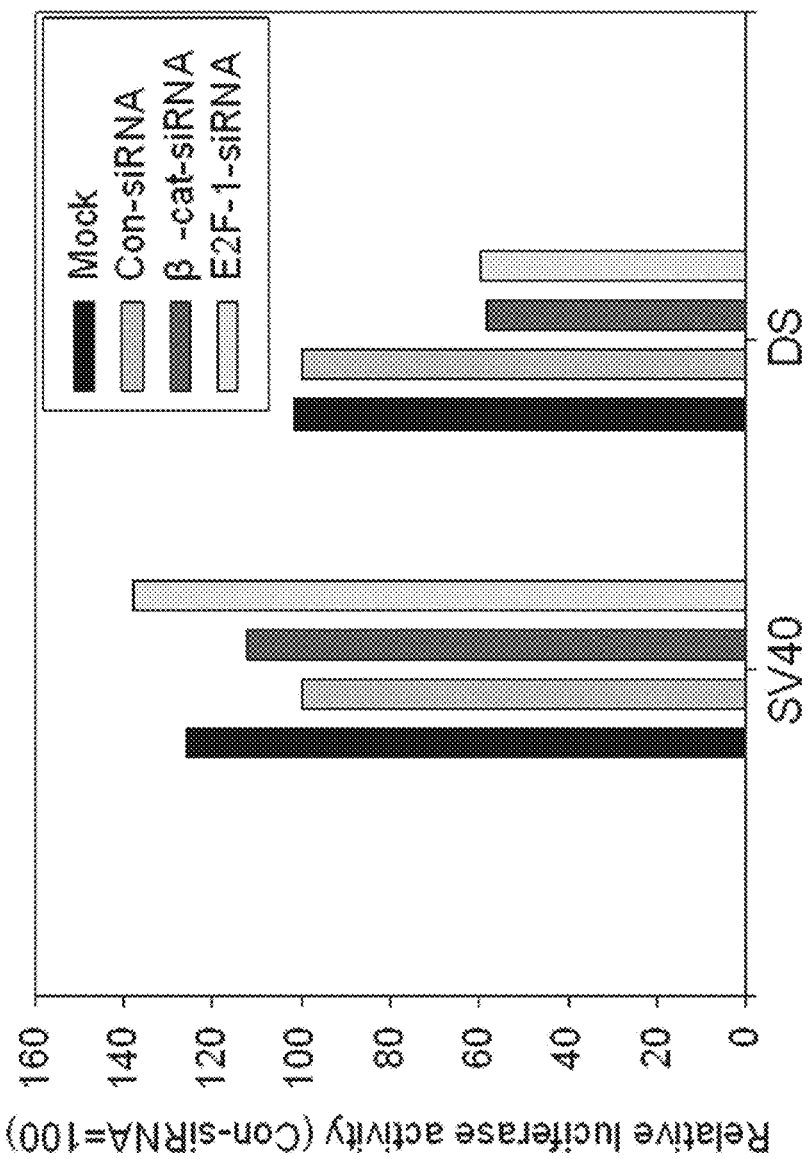
FIG. 5B: relative luciferase activities which converted the relative values of FIG. 5A based on assumption that the value obtained when treating with control siRNA is 100.

In order to investigate the relationship between the DS promoter activity and genetic environment, siRNAs were used. A549 cells were cultured in a E-well plate to reach 60% confluency and the medium was replaced with opti-MEM medium. The cells were then transfected with 250 μmol of E2F-1 siRNA (SEQ ID NO: 15) and β-catenin siRNA (SEQ ID NO: 16) using lipopectamine 2000 (Invitrogen, CA), respectively. After incubation in 37° C., 5% $CO_2$ for 6 hours, the medium was replaced with DMEM medium supplemented with 10% FBS. The cells were transfected with phRL-DS vector according to the method described in Example <1-2>. After 48 hours of incubation, the luciferase activity induced by DS promoter was measured, which is shown in FIGS. 5A and 5B. FIG. 5A represents the relative luciferase activities induced by DS promoter and SV40 promoter, after treatment of siRNAs against β-catenin or E2F-1, and FIG. 5B shows the converted values of those in FIG. 5A based on assumption that the value obtained when treating with control siRNA is 100.

As a result, the DS promoter-induced luciferase activity was reduced to about 40% in A549 cells by treatment of siRNAs against E2F-1 and β-catenin, when compared to treatment of non-specific siRNA (FIG. 5B). However, no reduction of promoter activity by the inhibition of E2F-1 and β-catenin was observed in case of SV40 promoter as a negative control, which indicates that the activity of DS promoter is dependent on E2F-1 and β-catenin.

Figure 6A:
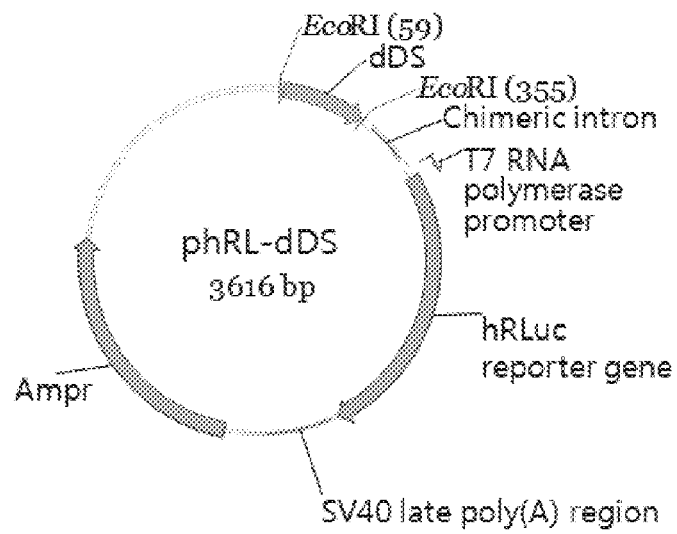
FIGS. 6A and 6B: cleavage maps of luciferase expression vectors comprising the E2F binding motif-deficient promoters dDS and dDL, respectively.
Figure 6B:
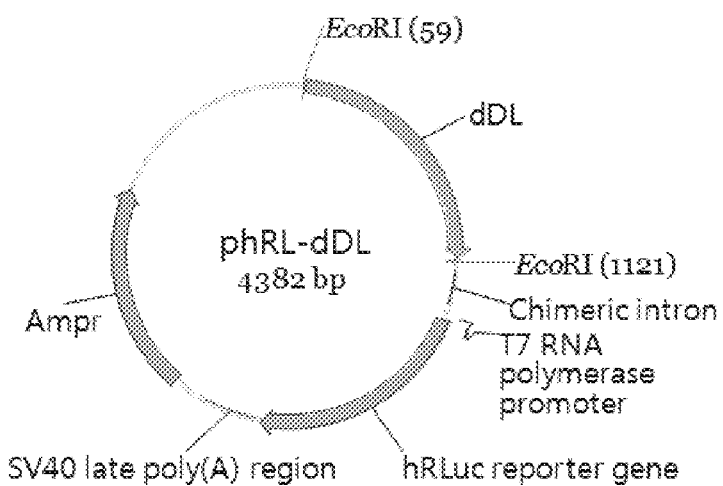
Figure 7:
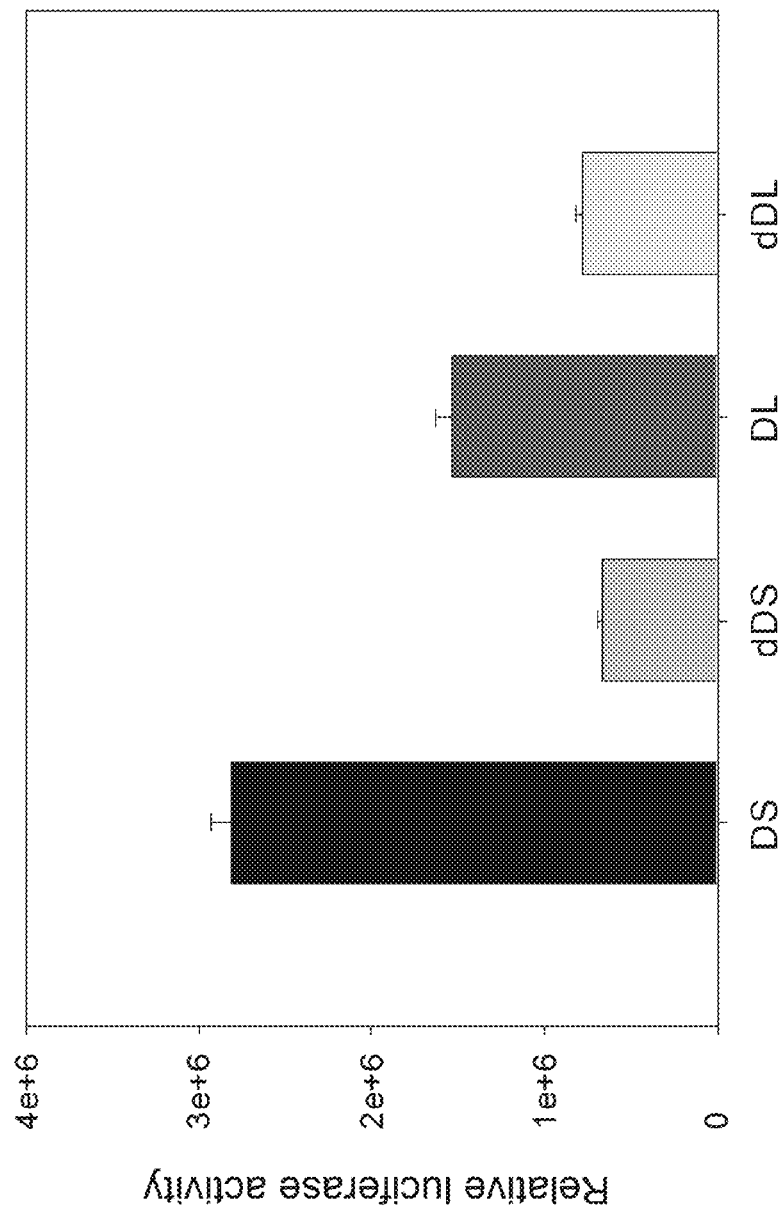
FIG. 7: relative luciferase activities induced by DS promoter, DL promoter, and E2F binding motif-deficient promoters dDS and dDL.

In order to examine how the E2F transcription factor binding motif present in DS promoter affects the activity of DS or DL promoter, dDS and dDL promoters where the E2F binding motif is deleted were constructed. Specifically, a luciferase vector phRL-dDS which contains dDS promoter (SEQ ID NO: 13) was constructed by the method described in Example <1-1> using sense and antisense primers of SEQ ID NOs: 1 and 7 (FIG. 6A). By the same method, a luciferase vector which contains dDL promoter (SEQ ID NO: 14) was constructed using sense and antisense primers of SEQ ID NOs: 5 and 7 (FIG. 6B). The constructed vector phRL-dDS and phRL-dDL, and phRL-DS and phRL-DL for comparison were transfected into A549 cells, respectively, as the method described in Example <1-2>. After 48 hours of incubation, the luciferase activities induced by each promoter were measured and the results are shown in FIG. 7. As shown in FIG. 7, the luciferase activity induced by dDS promoter was decreased about 80% compared to that induced by DS promoter, and the activity induced by dDL promoter was decreased about 50% compared to that of DL promoter. These results suggest that the binding between the promoter and the E2F transcription factor is significant to the DS or DL promoter activity.

Example 2

Construction of Adenovirus Vector Containing the Tumor-Specific Promoter and Adenovirus Using the Same <2-1> Construction of Adenovirus Vector Shuttle vectors required for the construction of adenovirus vector were constructed as follows. pENTR2B vector (Invitrogen, CA) was digested with EcoRI to remove ccdB region. After pAAV-CMV_LK8_UN plasmid prepared by the present inventors (see WO2009/102085) was digested with KpnI/BglII (blunted later) to obtain CMV_LK8 fragment, the CMV_LK8 fragment was inserted into pENTR2B vector digested with KpnI/XhoI(blunted later) to construct pENTR-CMV_LK8.

Meanwhile, pCR-DS prepared in Example <1-1> was digested with SacI and XhoI and the obtained fragment was inserted into pSP72-E2F_mE1A_ΔE1B19K (mE1A: see Korean Patent No. 746122; ΔE1B19K: see Korean Patent No. 432953) digested with ClaI and SalI to construct pSP72-DS_mE1A_ΔE1B19K.

In addition, pCR-5'E2F prepared in Example <1-1> was digested with BamHI (blunted later) and EcoRV and the obtained fragment was inserted into pSP72-DS_mE1A_ΔE1B19K plasmid digested with SpeI (blunted later) to construct pSP72-5'ED_mE1A_ΔE1B19K.

Figure 8A:
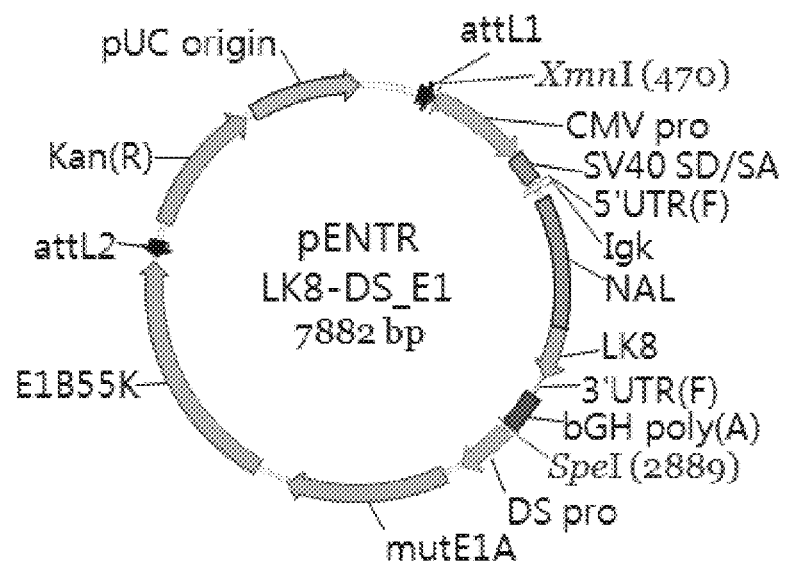
FIGS. 8A to 8D: cleavage maps of shuttle vectors comprising the tumor-specific promoter or LK8 gene.
Figure 8B:
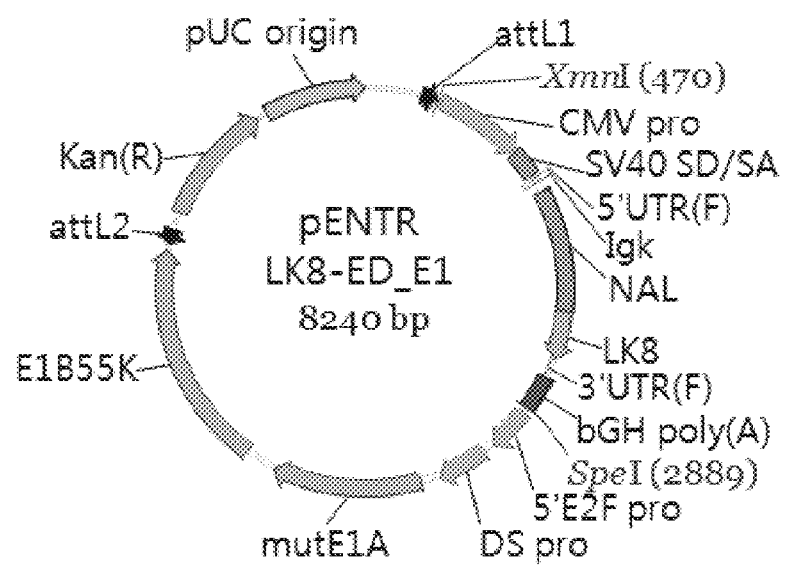
Figure 8C:
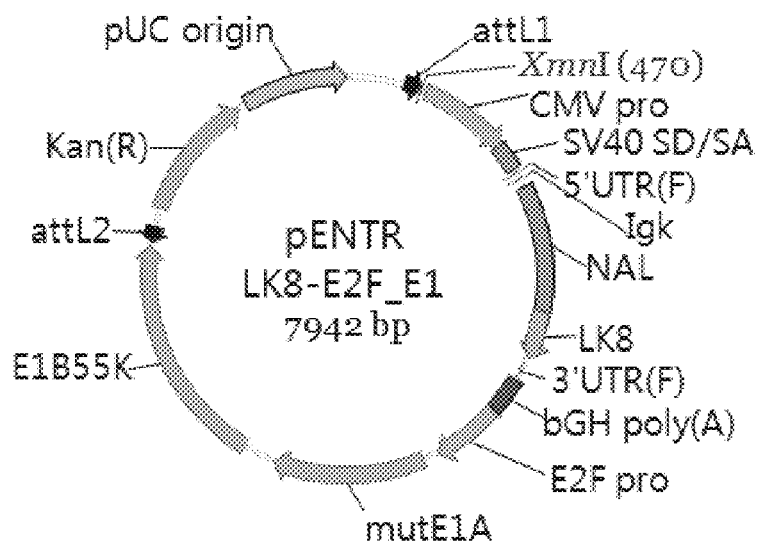

Finally, the pSP72-DS_mE1A_ΔE1B19K, pSP72-5'ED_mE1A_ΔE1B19K and pSP72-E2F_mE1A_ΔE1B19K plasmids were digested with BamHI, respectively, and each resultant fragment was inserted into pENTR-CMV_LK8 digested with BglII, to construct shuttle vectors pENTR-CMV_LK8-DS_mE1A_ΔE1B19K (pENTR-LK8-DS_E1), pENTR-CMV_LK8-5'ED_mE1A_ΔE1B19K (pENTR-LK8-ED_E1), and pENTR-CMV_LK8-E2F_mE1A_ΔE1B19K (pENTR-LK8-E2F_E1), respectively (FIGS. 8A to 8C).

Figure 8D:
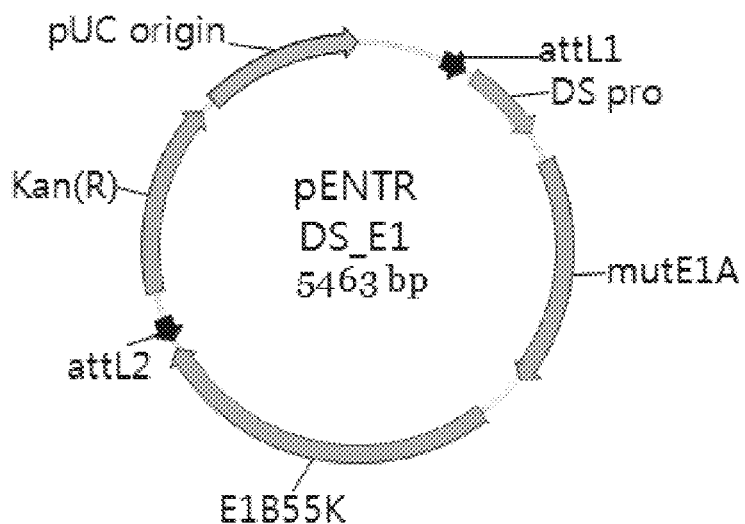

Further, the pENTR-LK8-DS_E1 was digested with XmnI and SpeI to remove CMV_LK8. The digested vector was blunted with klenow enzyme (NEB, MA) and self-ligated to construct pENTR-DS_mE1A_ΔE1B19K (pENTR-DS_E1) (FIG. 8D). The four shuttle vectors constructed above, pENTR-LK8-DS_E1, pENTR-LK8-ED_E1, pENTR-LK8-E2F_E1 and pENTR-DS_E1 were inserted into adenovirus vector pAd/PL-Dest (Invitrogen, CA), respectively, using LR clonase (Invitrogen, CA) as follows. Specifically, 300 ng of each shuttle vector and 100 ng of pAd/PL-Dest vector were mixed, 16 μL of clonase I reaction buffer (Invitrogen, CA) and 2 μL of clonase I were added thereto sequentially, and the reaction was performed at 25° C. for 1 hour. And then, 2 μL of proteinase K (2 μg/μL) was added thereto and the reaction was performed at 37° C. for 10 min. A competent cell such as DH5α was transformed with 10 μL of the resultant reaction solution and spread on an ampicillin-resistant plate. After purifying DNA from the transformant derived from a single colony, the presence of target adenovirus vector was confirmed by the mapping using restriction enzymes and the sequence analysis and the adenovirus vectors were designated as "pAd/PL-8DS," "pAd/PL-8ED," "pAd/PL-8E2F" and "pAd/PL-DS," respectively (FIGS. 9A to 9D).

<2-2> Preparation and Purification of Tumor-Specific Recombinant Adenovirus

3 μg of each adenovirus vector constructed in Example <2-1> was digested with PacI and transfected into A549 cells grown at 2×10⁵ cells/well in a 6-well plate using Jet-PEI (Polyplus, France). After incubation for 48 hours, the cells were subcultured in a 100 mm² petri dish by replacing 10 mL of DMEM/10% FBS every two days. When the cytopathic effect (CPE) appeared in 10 days after transfection, cells and medium were collected, followed by freezing and thawing (Δ2) to lyse the cells. The cell lysates were centrifuged at 3000 rpm for 5 min. The resultant supernatant was sequentially diluted from $10^{-4}$ to $10^{-9}$ and 200 μL of the diluted supernatant was added to a 6-well plate where A549 cells are grown at 2×10⁵ cells/well. After incubation for one hour, the medium was removed, 3 mL of 1.5% Agarose/DMEM/10% FBS was overlaid onto the cell layer, and 1 mL of 1.5% Agarose/DMEM/10% FBS was added every two or three days. 10 to 14 days later, ten plaques per each virus (rAd/PL-8DS-1~10, rAd/PL-8ED-1~10, rAd/PL-8E2F-1~10 and rAd/PL-DS-1~10) were collected and suspended in 1 mL of DMEM medium at 4° C., and 500 μL of the plaque suspension solution was added to a 100 mm² petri dish where A549 cells are grown at 2×10⁶ cells/well. When the cytopathic effect appeared in about 3 or 5 days after transfection, cells and medium were collected, followed by freezing and thawing (Δ2) to lyse the cells. The cell lysates were centrifuged at 3000 rpm for 5 min. The resultant supernatant was filtered using 0.45 μm of syringe filter (Millex-GV, Millipore) and the obtained viruses were designated "A(0) virus" (rAd/PL-8DS-1~10_A(0), rAd/PL-8ED-1~10_A(0), rAd/PL-8E2F-1~10_A(0) and rAd/PL-DS-1~10_A(0), respectively).

The adenoviral titers of A(0) viruses were measured by using QuickTiter™ Adenovirus titer immunoassay kit (Cell Biolabs). Specifically, 10-fold serial dilutions of each virus from $10^{-4}$ to $10^{-7}$ were performed and added to a 24-well plate where HEK293 cells are grown at 4×10⁴ cells/well. After incubation for two days, the medium was removed, and the cells were fixed by adding 0.5 mL of 100% methanol (Merck) and washed 5 times with 1× PBS. Then, the cells were blocked for 1 hour by adding thereto 1% BSA/PBS, and incubated for 1 hour after 0.25 mL of 1× anti-Hexon antibody solution was added thereto. The cells were washed three times with 1×PBS, and incubated for 1 hour after 0.25 mL of 1×HRP-conjugated Secondary antibody solution was added thereto. The cells were again washed three times with 1×PBS, and incubated for 1030 minutes after 0.25 mL of 1×DAB working solution was added thereto for staining. The number of stained cells was counted using a microscope. The adenoviral titer (infectious units/mL; IFU/mL) was calculated by following equation, in which N indicates the number of stained cells observed by a microscope with 100× total magnification (Field Area: 2.54 mm²) in a 24-well plate (Well Area: 2.0 cm²).

$$\text{IFU/mL}=(N\times 79(\text{well area/field area})\times \text{dilution factor})/(0.1\text{ mL})$$

Figure 10:
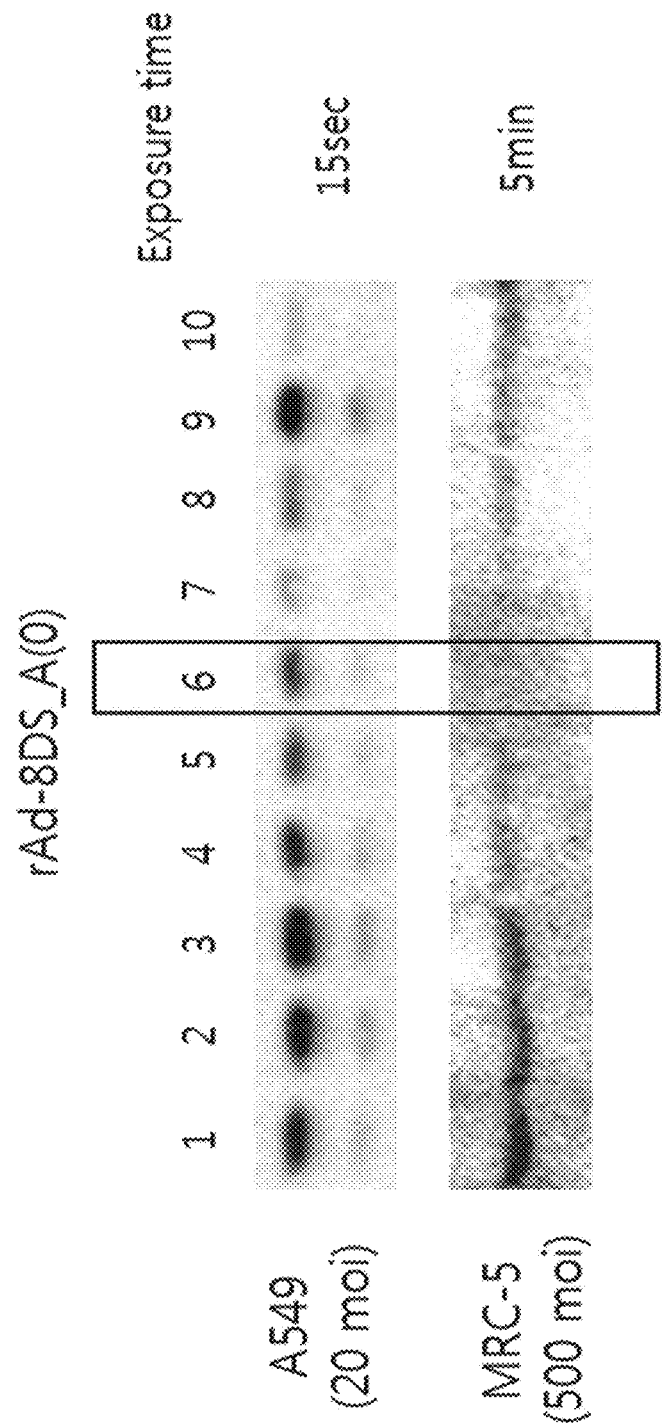
FIG. 10: E1A expression levels induced by the tumor-specific promoters in a normal cell line (MRC-5) and a tumor cell line (A549), which are determined by western blot after infecting MRC-5 and A549 with rAd-8DS_A(0) at 500 and 20 m.o.i (multiplicity of infection), respectively.

A549 and MRC-5 cells grown at 4×10⁴ cells/well in a 24-well plate were infected with rAd-8DS-1~10_A(0) (MOI=10, based on IFU measured above). On day 1 after infection, each cell was harvested, and the expression of adenoviral E1A gene was detected by Western blotting using Ad5 E1A antibody (BD Pharmingen). By comparison of detected E1A expressions in rAd-8DS-1~10_A(0), a virus clone, rAd-8DS-6_A(0) which shows a high E1A expression level in A549 cells (tumor cells) compared to MRC-5 cells (normal cells), was selected (FIG. 10). Likewise, in case of other viruses, clones rAd-DS-7_A(0), rAd-8ED-6_A(0) and rAd-8E2F-1_A(0) were selected based on E1A expression by Western blotting. The selected viruses were used for mass production below.

A549 cells grown at 2×10⁷ cells in thirty (30) T175 mm² flasks were infected with the A(0) viruses (MOI=5) selected above. When the cytopathic effect appeared in two days after infection, all cells were harvested, suspended in 20 mL of a cell lysis buffer (500 mM Tris, 1 mM MgCl₂, pH 8.0), followed by freezing and thawing (Δ3) to lyse the cells. The cell lysates were centrifuged at 3000 rpm for 5 min. The resultant supernatant was filtered sequentially through 0.8 μm (Millex-AA, Millipore) and 0.22 μm (Millex-GV, Millipore) of syringe filters, treated with benzonase (250 U/μL, Novagene) in a final concentration of 10 U/mL, and incubated at 37° C. for 30 min.

The viruses prepared above were purified by double CsCl Gradient method. First, 8 mL of a cesium chloride solution of density 1.4 (53 g CsCl, 87 mL 10 mM Tris-HCl, pH 7.9), 6 mL of a cesium chloride solution of density 1.2 (26.8 g CsCl, 92 mL 10 mM Tris-HCl, pH 7.9) and the cell lysate were sequentially overlaid in a centrifuge tube. The tube was then centrifuged at 23,000 rpm (100,000×g), 4° C. for 90 min by using a SW28 rotor (Beckman) and an ultracentrifuge (XL-70, Beckman). After centrifugation, a whitish virus band was collected using an 18G needle. An equivalent or higher volume of 1×TE buffer was again added thereto, and subjected to the ultracentrifugation as described above. The virus pellets were dialyzed all day in a storage buffer (1 mM MgCl₂, 10% glycerol/PBS) using a Slide-A-Lyzer® Dialysis Cassette 10K membrane (Pierce Biotechnology) equilibrated with PBS. After replaced with a new storage buffer, the viruses were again dialyzed for 4 hours, seeded, and designated "A(1) virus" (rAd-8DS-6_A(1), rAd-8ED-6_A(1), rAd-8E2F-1_A (1) and rAd-DS-7_A(1)).

The physical particle titer of the virus purified above was calculated by measurement of optical density. 30% and 80% of virus dilutions were prepared, incubated at room temperature for 20 min, and OD value was measured at 260 nm using an UV spectrophotometer (DU650, Beckman). The physical particle titer of the adenovirus (VP/mL) was calculated by following equation.

$$VP/mL = A_{260} \times (1.1 \times 10^{12} \text{ particles/mL}) \times (1/\text{dilution factor})$$

Example 3

In Vitro Oncolytic Effects of the Recombinant Viruses

The oncolytic effects of the recombinant adenoviruses prepared in Example <2-2> were investigated by the cytopathic effect (CPE) method. Specifically, normal cells such as MRC-5, WI38 and SAEC, and tumor cells such as A549, H358, H460, H596, H2172, C33A, Hep3B, DU145, Miapaca-2, MDA-MB231 and U2OS, which were grown at $1 \times 10^4$ cells/well in a 48-well plate, were infected with the recombinant viruses at 20 to 0.005 MOI based on IFU by serial-dilutions. The oncolytic effects of the viruses were examined by the staining of the survived cells with a crystal violet solution on day 10 after infection for normal cells and on day 7 after infection for tumor cells. As controls, an adenovirus rAd-mE1A_ΔE1B19K (rAd-Rb7Δ19) (see Korean Patent Nos. 432953 and 746122) and rAd-LacZ where E1A was replaced with LacZ were used.

Figure 11:
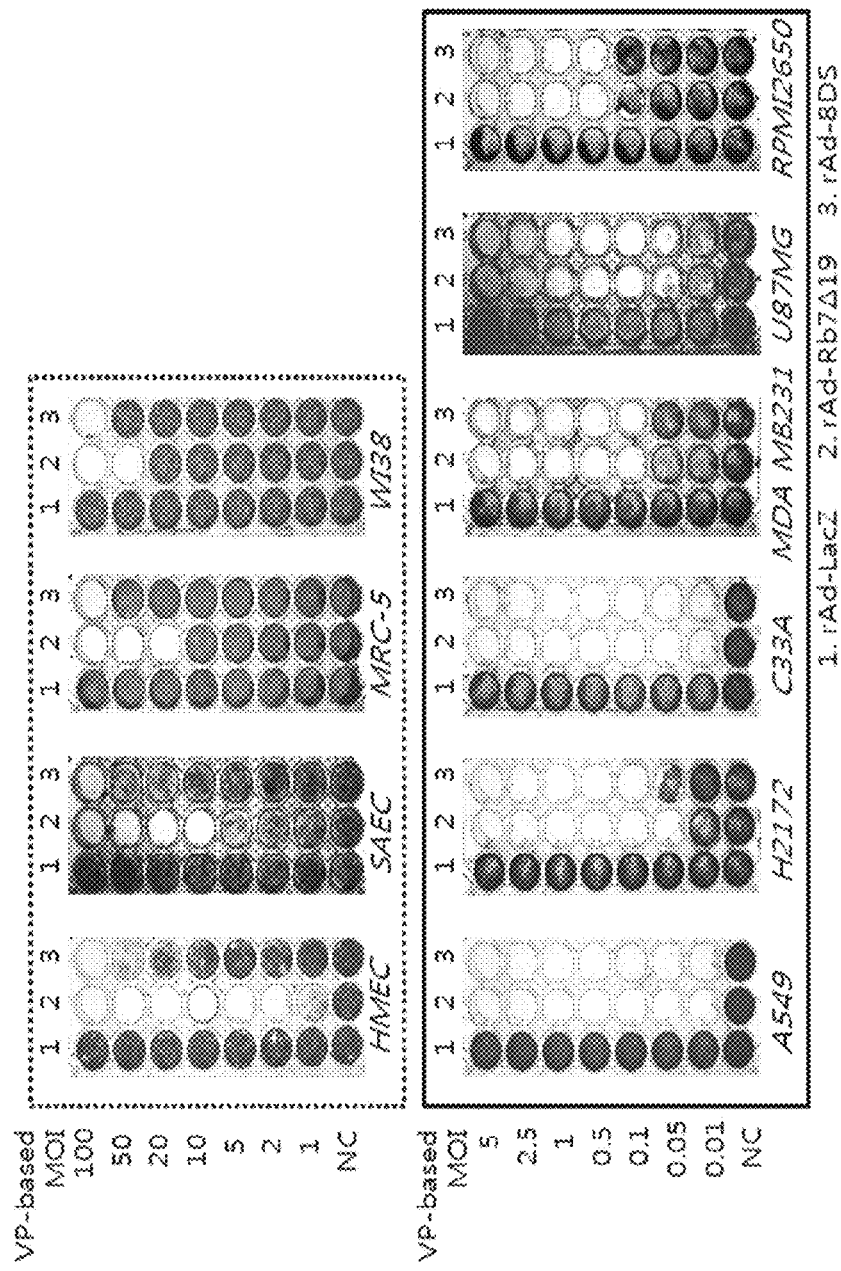
FIG. 11: a CPE analysis result showing tumor-specific oncolytic effect of rAd-8DS in normal cell lines (HMEC, SAEC, MRC-5 and WI38) and tumor cell lines (A549, H2172, C33A, MDA-MB231, U87MG and RPMI2650) infected with the serial dilutions of rAd-LacZ control, rAd-Rb7Δ19 and rAd-8DS.
Figure 12:
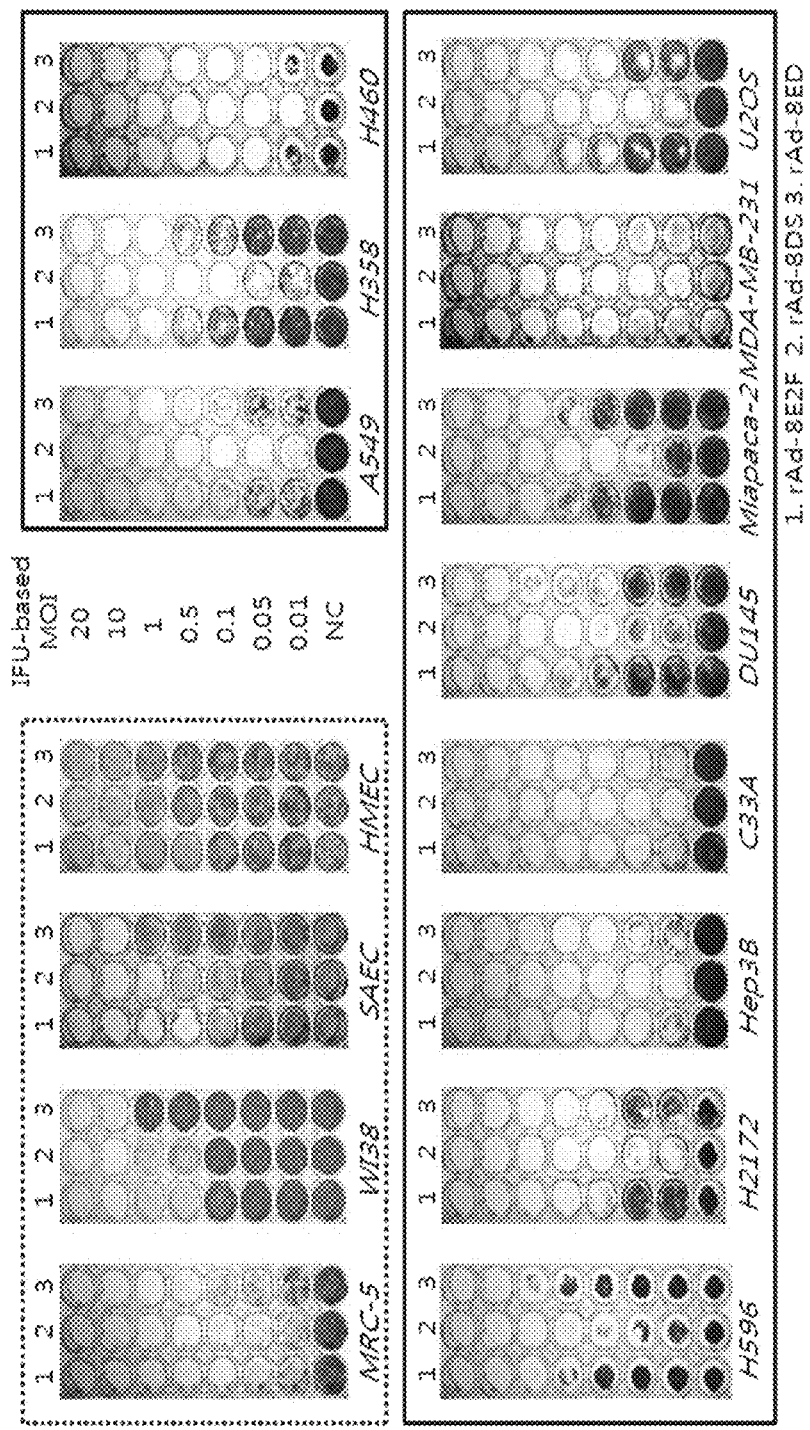
FIG. 12: a CPE analysis result showing lytic activities of oncolytic adenoviruses (rAd-8E2F, rAd-8DS and rAd-8ED)

The results are shown in FIGS. 11 and 12. As shown in FIG. 11, the oncolytic activity (cytotoxicity) of rAd-8DS was 5 to 10 times lower than that of rAd-mE1A_ΔE1B19K (rAd-Rb7Δ19) in normal cells, but was similar to that in tumor cells, which demonstrates that the tumor-specific oncolytic activity increased to 5 to 10 times by the introduction of DS promoter. Meanwhile, as shown in FIG. 12, DS promoter induced equivalent or 2 to 5 times lower oncolytic activity than E2F promoter in normal cells, but 5 to 10 times higher in tumor cells. In addition, 5'ED promoter showed about 10 times lower oncolytic activity than E2F promoter in normal cells, but equivalent to that in tumor cells. These results indicate that the tumor cell selectivity of DS promoter and 5'ED promoter is about 10 times superior to that of E2F promoter previously established.

Example 4

In Vivo Anticancer Effects of Recombinant Adenoviruses

Figure 13A:
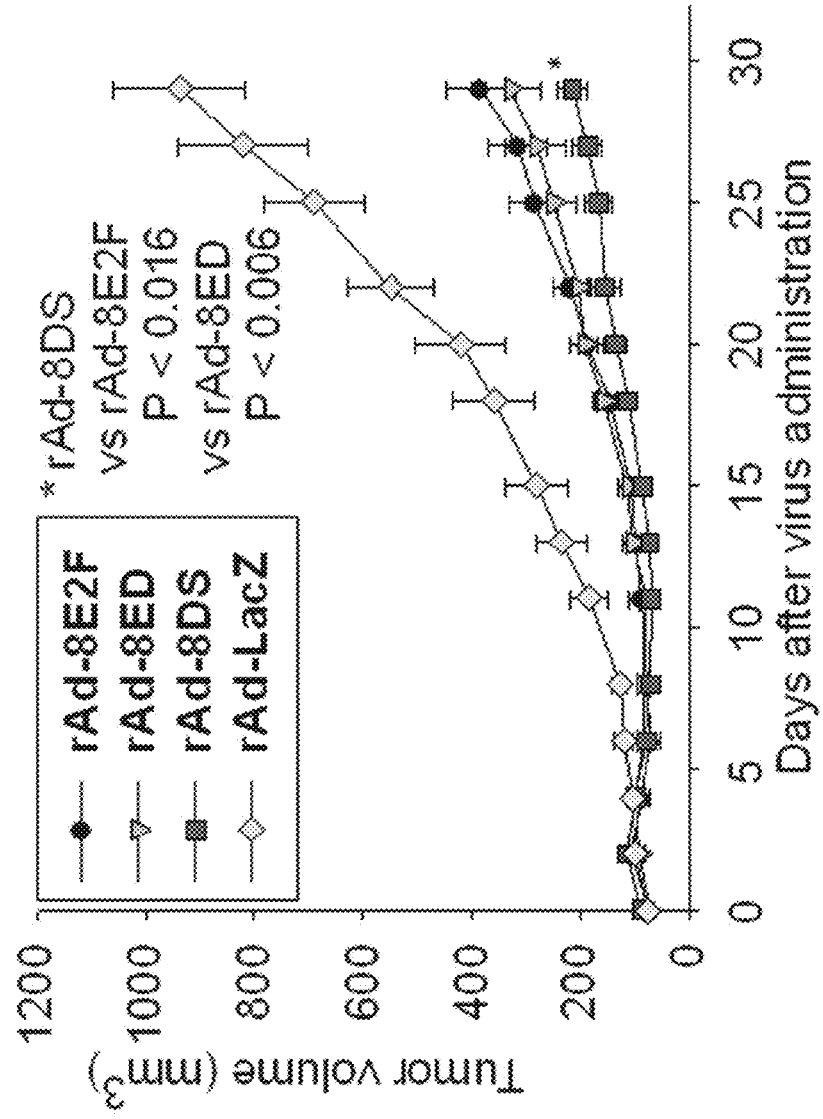
FIGS. 13A and 13B: antitumor activities of oncolytic adenoviruses (rAd-8E2F, rAd-8ED, rAd-8DS and rAd-LacZ) in a lung cancer (H2172) heterotropic transplantation model, in which (A) and (B) exhibit the tumor size and the survival rate of mice, respectively.
Figure 13B:
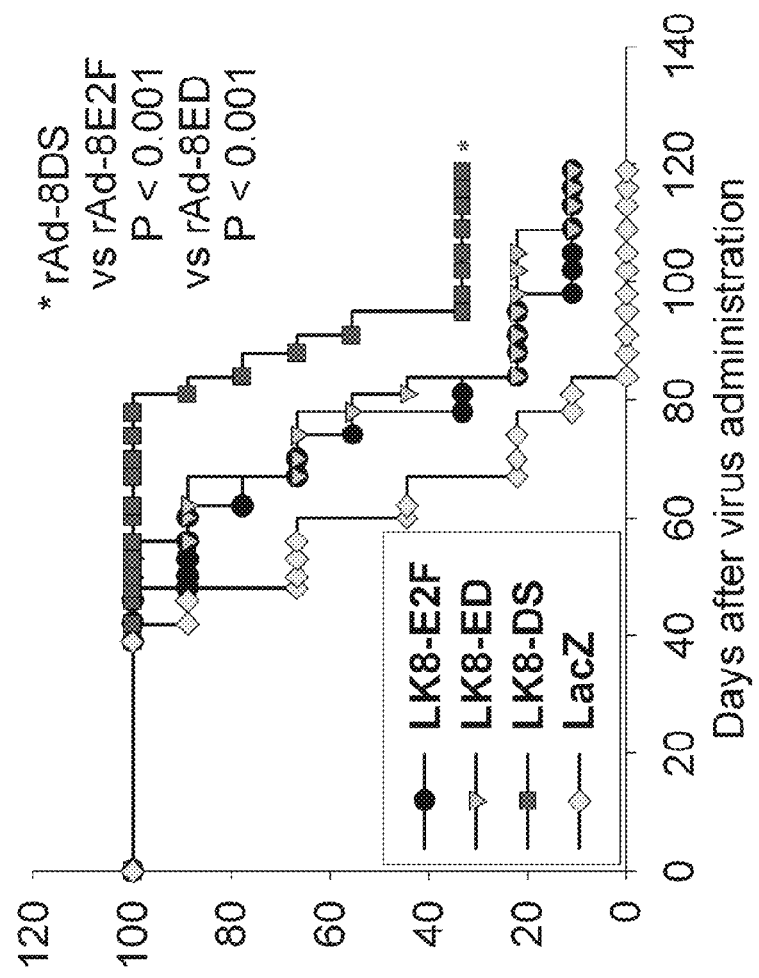

<4-1> Oncolytic Effects of the Tumor-Specific Promoters in a Lung Cancer Heterotropic Transplantation Model $5 \times 10^6$ cells of non-small cell lung cancer cell lines, NCI-H2172, were subcutaneously injected on the flank of immuno-deficient mice to form 50-100 mm³ of tumors. After tumor formation, the mice were divided into four groups, each group having 14 mice. The mice of each group were administered with rAd-LacZ, rAd-8E2F, rAd-8DS and rAd-8ED, respectively, in a concentration of $1 \times 10^9$ IFU/mL three times in two day interval, followed by observation of the tumor size and the survival rate of mice. The results are shown in FIGS. 13A and 13B. In case of the tumor cell growth, on day 29 after administration of viruses, rAd-8E2F, rAd-8ED and rAd-8DS showed 59%, 65% and 77% of the inhibition rate of tumor cell formation compared to a control, rAd-LacZ, respectively. rAd-8E2F and rAd-8ED showed no significance by Student's t-test, but rAd-8DS showed the significances of P<0.016 and P<0.006 with Ad-8E2F and Ad-8ED, respectively (FIG. 13A). In case of the survival rate, median survival times in rAd-LacZ, rAd-8E2F, rAd-8ED and rAd-8DS groups were 60 days, 78 days, 81 days and 95 days, respectively. In particular, rAd-8DS was most excellent in that the increase of median survival time is 58% compared to rAd-LacZ. In the statistical significance, rAd-8DS showed significant values of P<0.001 with both rAd-8E2F and rAd-8ED (FIG. 13B).

Figure 14:
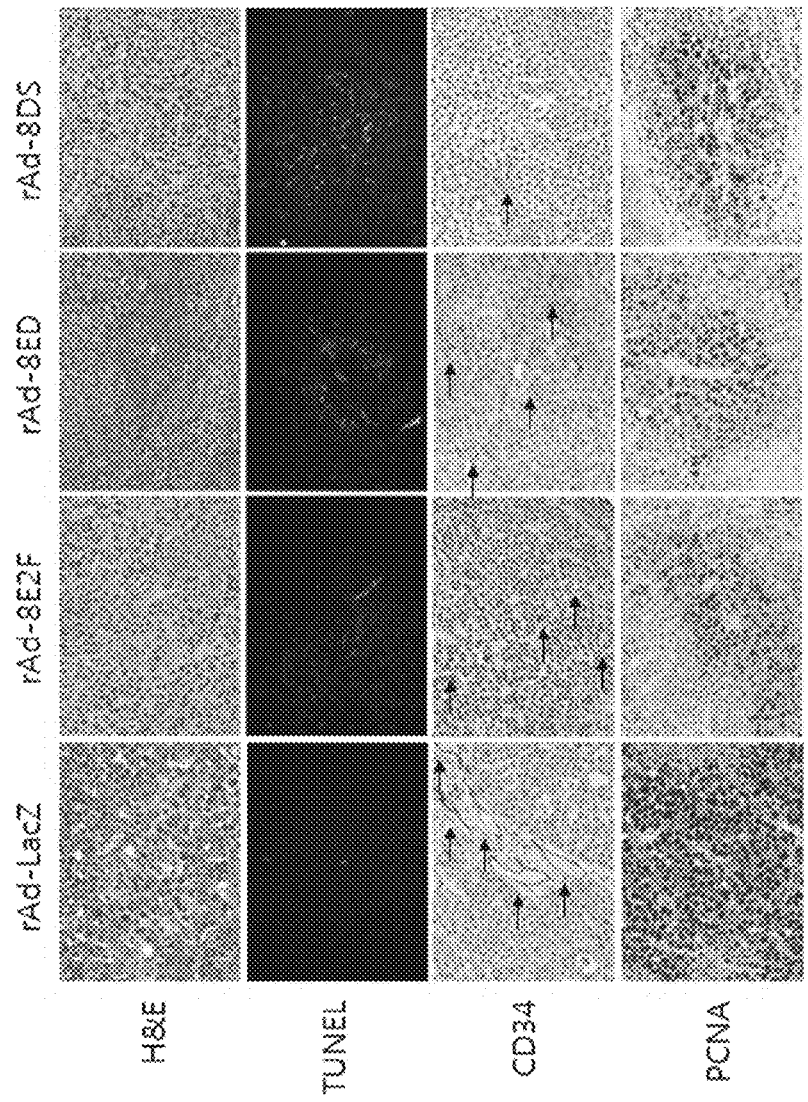
FIG. 14: an immunohistochemical result of cytosol and nucleus (H & E), apoptotic cell (TUNNEL), vascular-associated tissue (CD34), and proliferating cell (PCNA) of a mouse model infected with the oncolytic adenoviruses.

In addition, tumor tissues of mice were analyzed using the immunochemical staining. Cytoplasm and nucleus were identified by H&E staining, number of death cells was identified by TUNEL assay, vascular endothelial cells were identified using CD34 antibody, and proliferating cells were detected by PCNA staining (Wada H et al., Oncology Report, (2007) 18:801). As shown in FIG. 14, mice administered with rAd-8DS, rAd-8E2F and rAd-8ED, respectively, showed the cell death facilitation, angiogenesis inhibition and cell proliferation inhibition when compared to mice administered with rAd-LacZ in tumor cells. Particularly, in the mice administered with rAd-8DS compared to those administered with rAd-8E2F or rAd-8ED, the cell death was more facilitated.

Figure 15B:
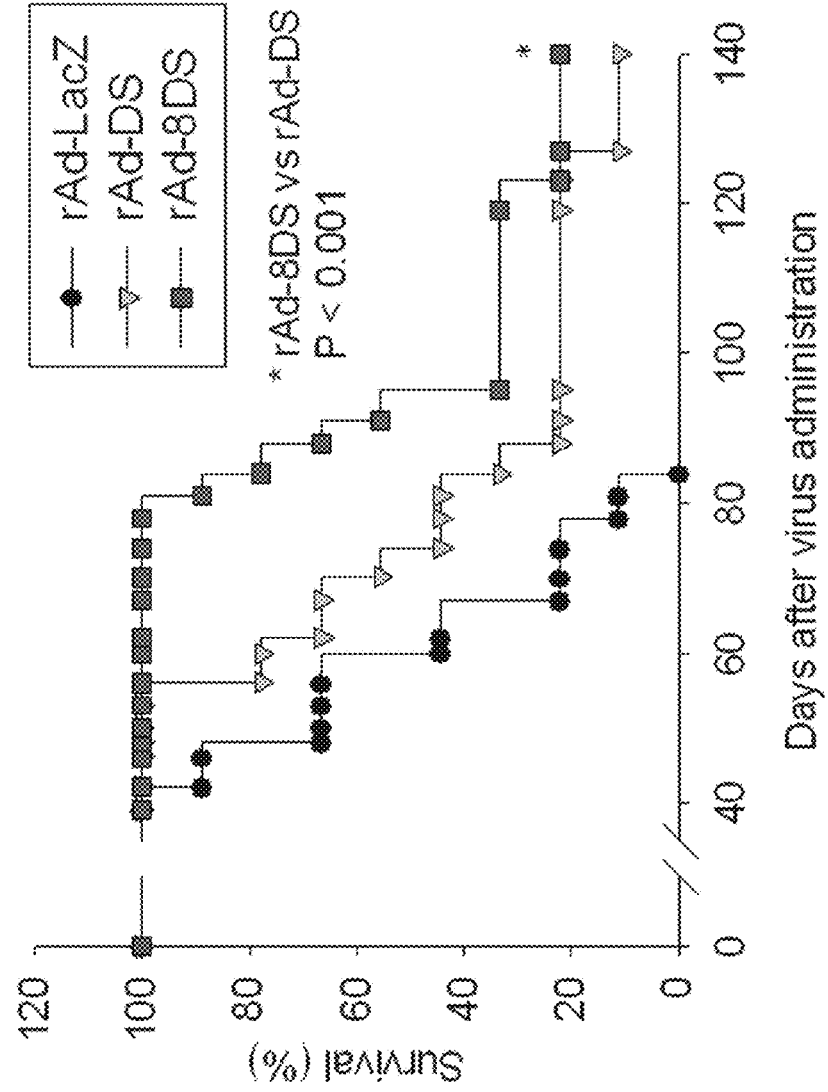

<4-2> Antitumor Effect in a Lung Cancer Heterotropic Transplantation Model by The Introduction of LK8 Gene Non-small cell lung cancer cell lines, NCI-H2172 were injected into immuno-deficient mice according to the method described in Example <4-1>. 14 mice of each group were administered with rAd-LacZ, rAd-DS and rAd-8DS, respectively, in a concentration of $1 \times 10^9$ IFU/mL three times in two day interval, followed by observation of the tumor size and the survival rate of mice. The results are shown in FIGS. 15A and 15B. In case of the tumor cell growth, on day 29 after administration of viruses, rAd-DS and rAd-8DS showed 57% and 77% of the inhibition rate of tumor cell formation compared to a control, rAd-LacZ, respectively, which demonstrate that the inhibition rate increased about 20% by introduction of LK8. Further, rAd-8DS showed the significance of P<0.004 with rAd-DS (FIG. 15A). In case of the survival rate, median survival times in rAd-LacZ, rAd-DS, rAd-8DS groups were 60 days, 74 days and 95 days, respectively, which demonstrates that the survival rate increased about 35% by introduction of LK8. Likewise, rAd-8DS showed significant values of P<0.001 with rAd-DS (FIG. 15B).

Figure 16A:
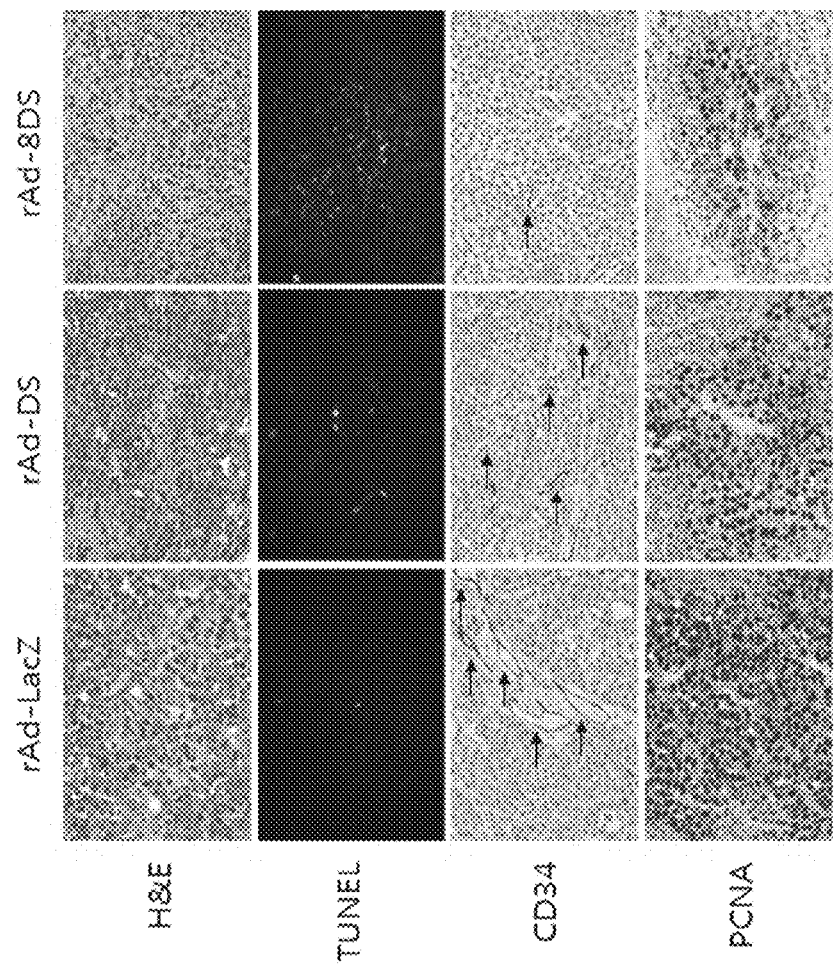
FIG. 16A: an immunohistochemical result when administering rAd-8DS and rAd-DS to a mouse model.
Figure 16B:
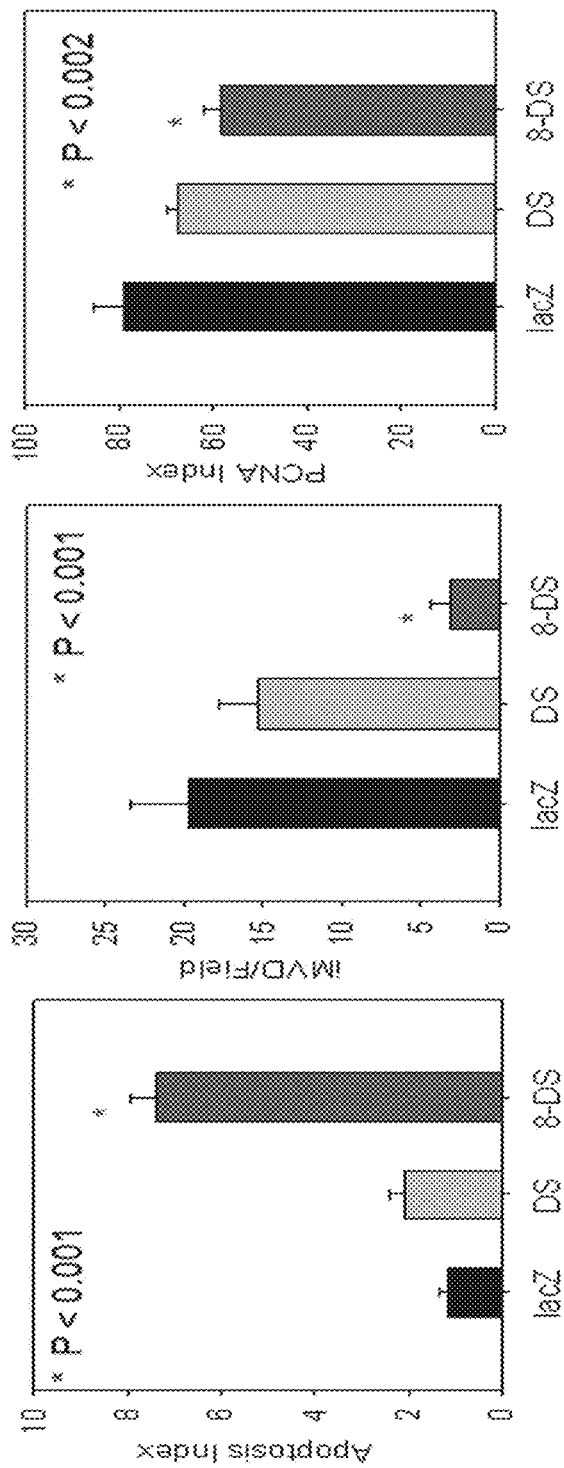
FIG. 16B: numbers of apoptotic cells, vascular cells, and proliferating cells, when administering rAd-8DS and rAd-DS to a mouse model, respectively.

Meanwhile, as a result of immunochemical staining, mice administered with rAd-8DS showed the increased cell death, angiogenesis inhibition and cell proliferation inhibition when compared to mice administered with rAd-DS in tumor cells (FIGS. 16A and 16B). These results confirm that the introduction of LK8 increased the antitumor activity.

<4-3> Antitumor Effect of rAd-8DS in a Lung Cancer Orthotropic Transplantation Model $1 \times 10^6$ cells of non-small cell lung cancer cell lines, NCI-H2172, were administered to immuno-deficient mice via tail vein injection, and one week later the mice were divided into 3 groups, each group having 10 mice. Each group was administered with $1 \times 10^{10}$ vp/mL of rAd-LacZ, rAd-DS and rAd-8DS, respectively, three times in two day interval, and 6 weeks later the lung was excised to examine the number of tumor nodules.

Figure 17A:
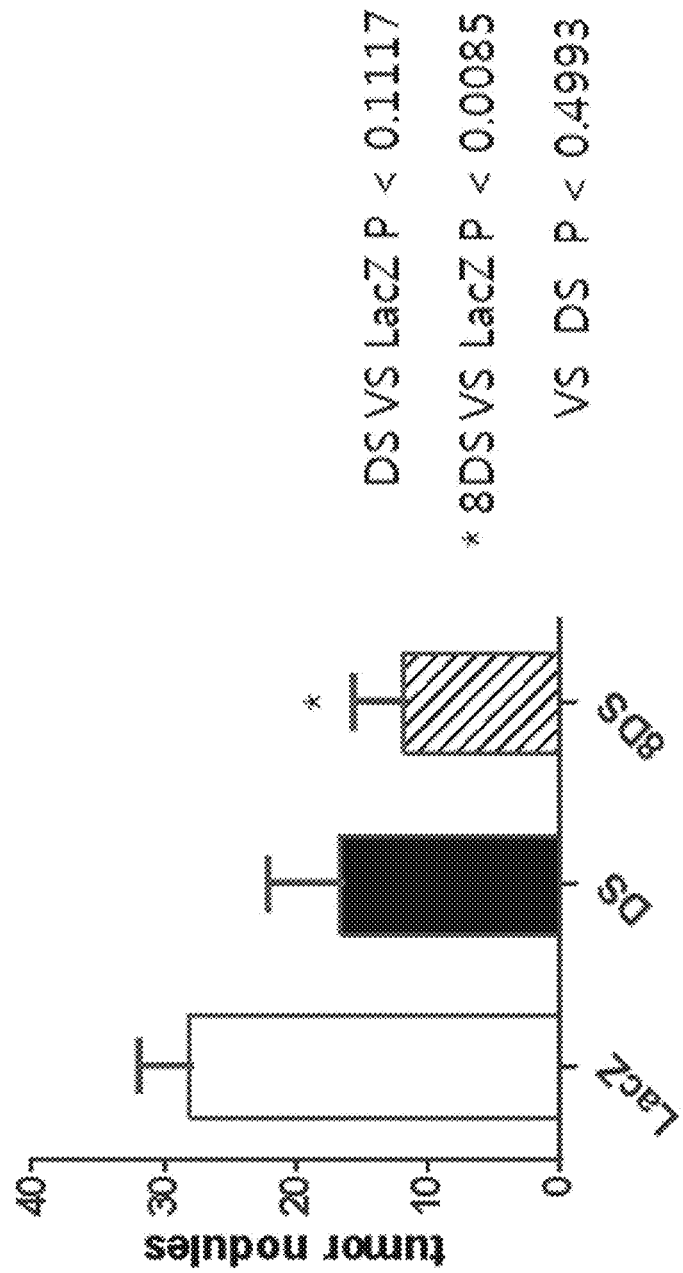
FIGS. 17A and 17B: the tumor nodule number (17A) and the immunohistochemical result obtained when administering rAd-8DS and rAd-DS to an orthotropic transplantation model (17B), respectively.
Figure 17B:
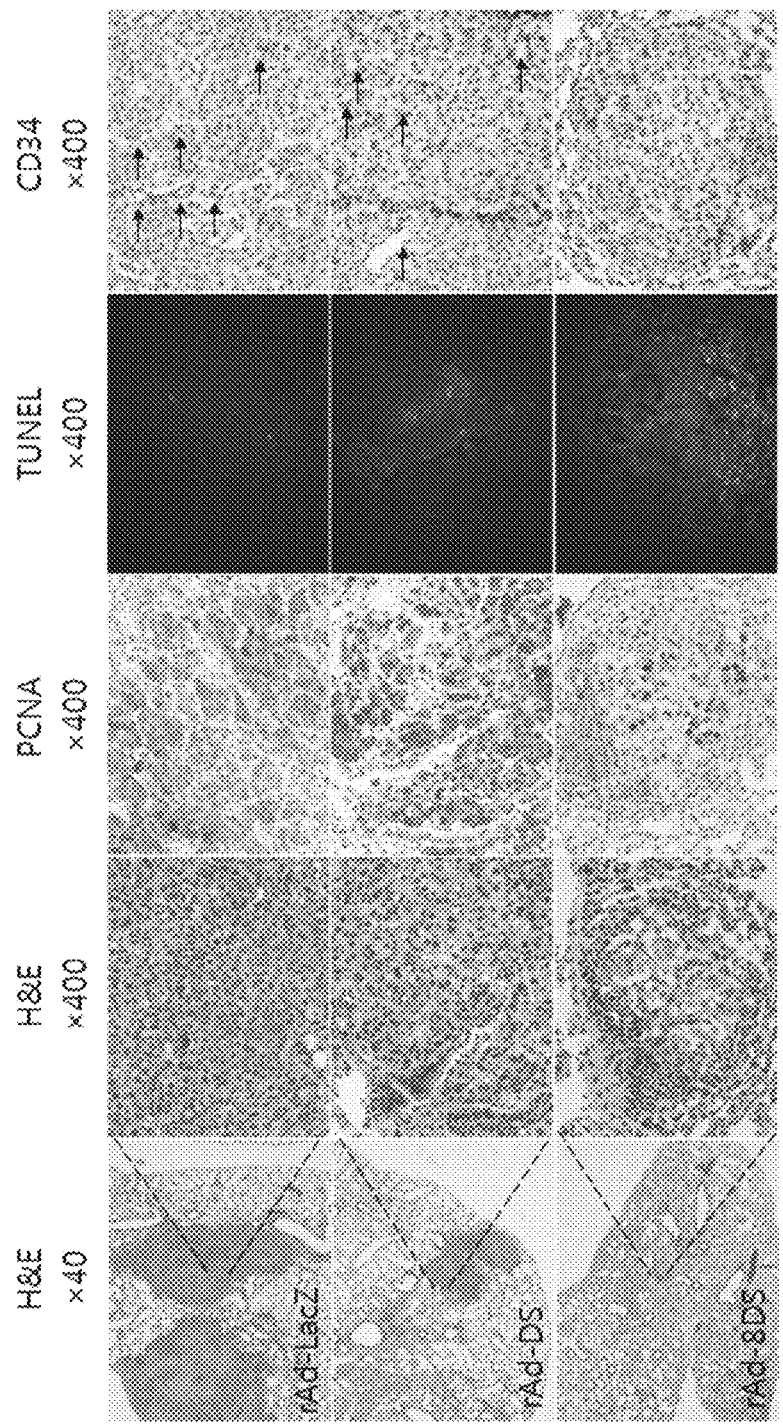

As a result, average 28, 17 and 12 tumor nodules were found in groups administered with rAd-LacZ, rAd-DS and rAd-8DS, respectively. As a result of statistical analysis, the group administered with rAd-DS showed no significance with that administered with rAd-LacZ, but rAd-8DS showed the significance (FIG. 17A). As a result of immunochemical staining, mice administered with rAd-8DS showed the increased cell death, angiogenesis inhibition and cell proliferation inhibition when compared to mice administered with rAd-DS in tumor cells (FIG. 17B). These results confirm that rAd-8DS has more superior antitumor effect to rAd-DS.

Figure 18A:
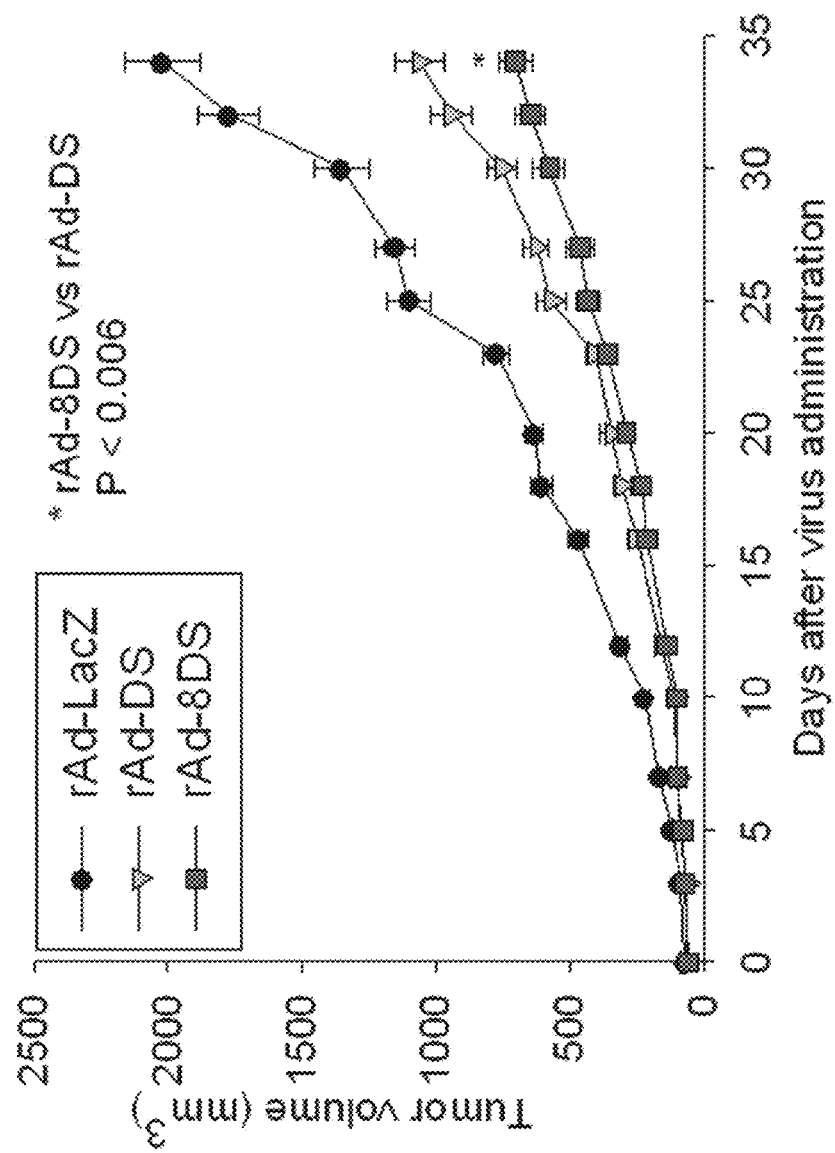
FIGS. 18A and 18B: antitumor activities of rAd-8DS and rAd-DS in a melanoma (A373SM) orthotropic transplantation model in terms of the tumor size (18A) and the survival rate (18B)
Figure 18B:
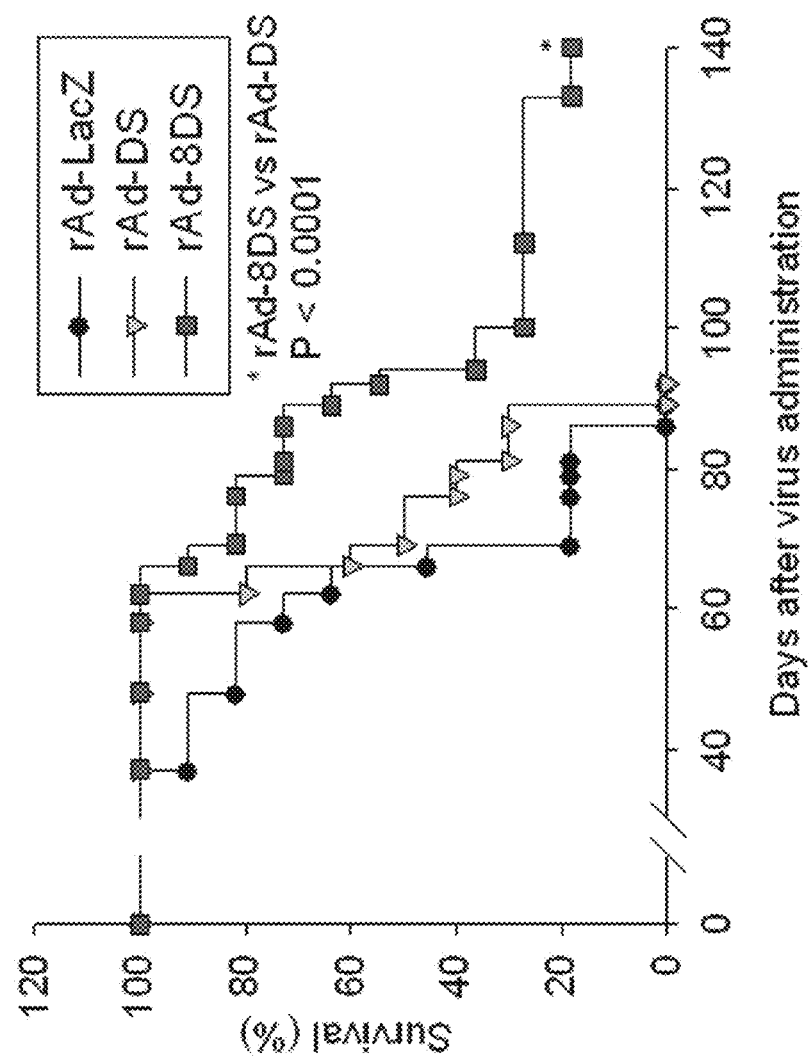

<4-4> Antitumor Effect of rAd-8DS in a Melanoma (A373SM) Orthotropic Transplantation Model $1\times10^6$ cells of melanoma cell lines, A373SM, were subcutaneously injected on the flank of immuno-deficient mice to form 50-100 mm³ of tumors, and the mice were divided into three groups, each group having 15 mice. The mice of each group were administered with $1\times10^{10}$ vp/mL of rAd-LacZ, rAd-DS and rAd-8DS, respectively, three times in two day interval, followed by observation of the tumor size and the survival rate of mice. In case of the tumor cell growth, on day 34 after administration of viruses, rAd-DS and rAd-8DS showed 47% and 65% of the inhibition rate of tumor cell formation compared to a control, rAd-LacZ, respectively (FIG. 18A). In case of the survival rate, median survival times in rAd-LacZ, rAd-DS and rAd-LK8-DS groups were 66 days, 72.5 days and 94 days, respectively, which indicates that median survival times increased 32.6% compared with the group administered with rAd-DS by the introduction of LK8 (FIG. 18B). In case of an immunochemical staining, mice administered with rAd-8DS showed the cell death facilitation, angiogenesis inhibition and cell proliferation inhibition when compared to mice administered with rAd-DS in tumor cells. These results confirm that the group of rAd-8DS has more superior antitumor activity to other groups (FIG. 18C).

Example 5

Construction of Adenovirus Substituted with the Fiber Protein of Serotype 35 (Ad35) and Measurement of Gene Delivery Efficiency It is respected that human adenoviruses currently known has different infection passages and an adenovirus serotype 5 (Ad5) which has been well investigated until now infects cells by the binding between cell receptors called CAR (Coxsackievirus-adenovirus receptor) expressed in a cell surface and the fiber protein of adenovirus. Viruses enter into a cell by the interaction between RGD motif (Arg-Gly-Asp) of adenoviral capsid protein, penton, and integrin protein in cells. Therefore, the infection efficiency of an adenovirus serotype 5 depends on the expression level of intracellular adenoviral receptor CAR and integrin. However, since the expression level of CAR and integrin is low in many cells including peripheral blood stem cells, dendritic cells, endothelial cells and malignant tumor cells, there exists problem that the infection efficiency rate of adenovirus serotype 5 is also relatively low. For these reasons, a study using other adenovirus serotypes is still going on.

Adenovirus serotype 35 infects cells via CD46 receptor instead of CAR, which is highly expressed in malignant cells such as breast cancers, colon cancers, and liver cancers. Therefore, the present inventors measured the gene delivery efficiency when the fiber protein of an adenovirus was substituted with that of adenovirus serotype 35.

<5-1> Construction of an Adenovirus Substituted with the Fiber Protein of Adenovirus Serotype 35

The fiber shuttle vector where the fiber protein of adenovirus serotype 35 is inserted thereinto was constructed. In order to visualize the infection activity against tumor cells by the substitution of the fiber protein, Ad-ΔE1/LacZ/35K non-replicant adenovirus, in which LacZ gene as labeling gene is inserted into E1 site and the fiber protein is altered with that of adenovirus serotype 35, was constructed.

<5-2> Comparison of Delivery Efficiency of Adenovirus in Various Cell Lines

Figure 20:
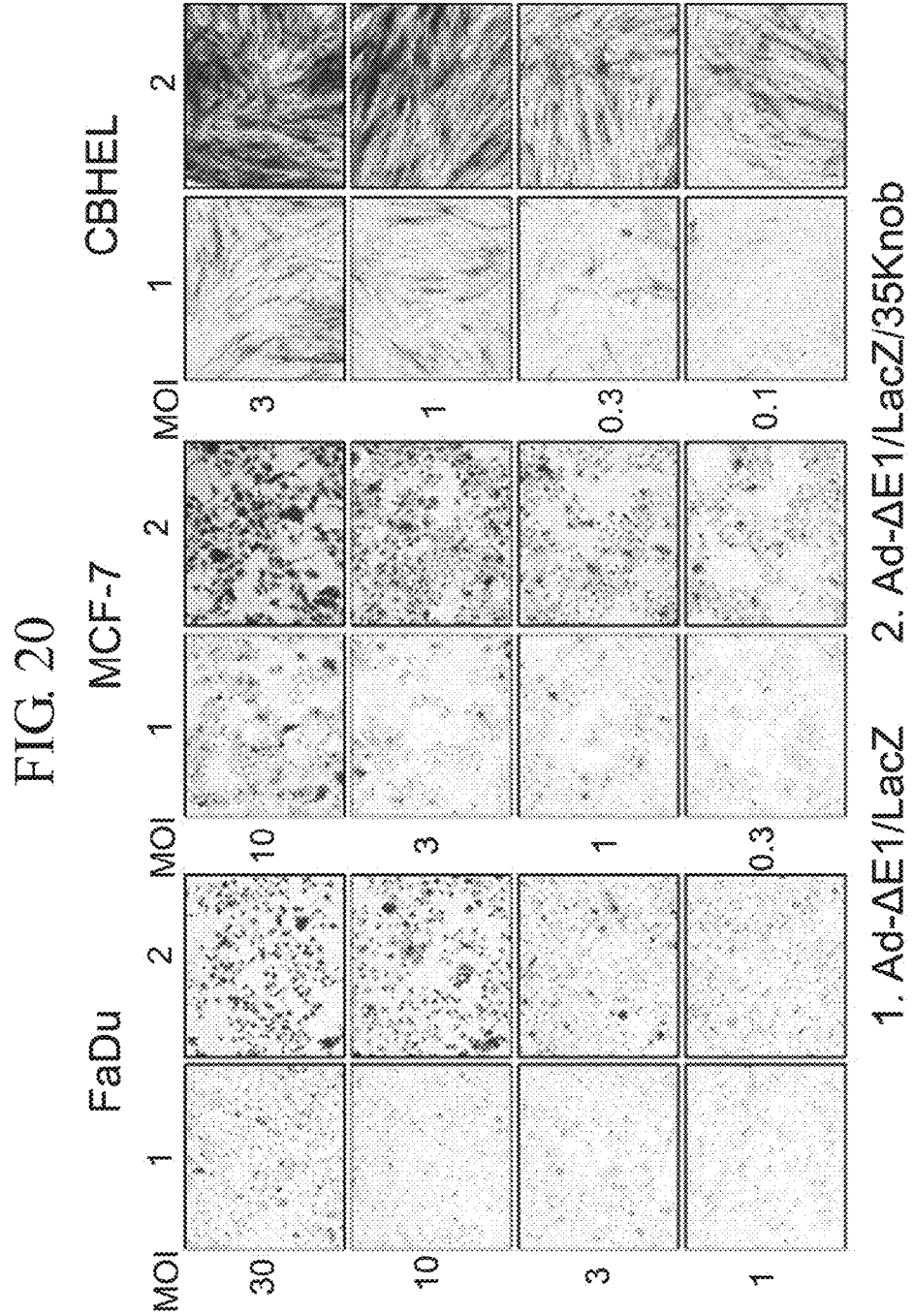
FIG. 20: gene transduction efficiencies according to LacZ expression, after infecting FaDu, MCF-7 and CBHEL cell lines with a control adenovirus (Ad-ΔE1/LacZ) and an adenovirus replaced with serotype 35 fiber (Ad-ΔE1/LacZ/35K)
Figure 21:
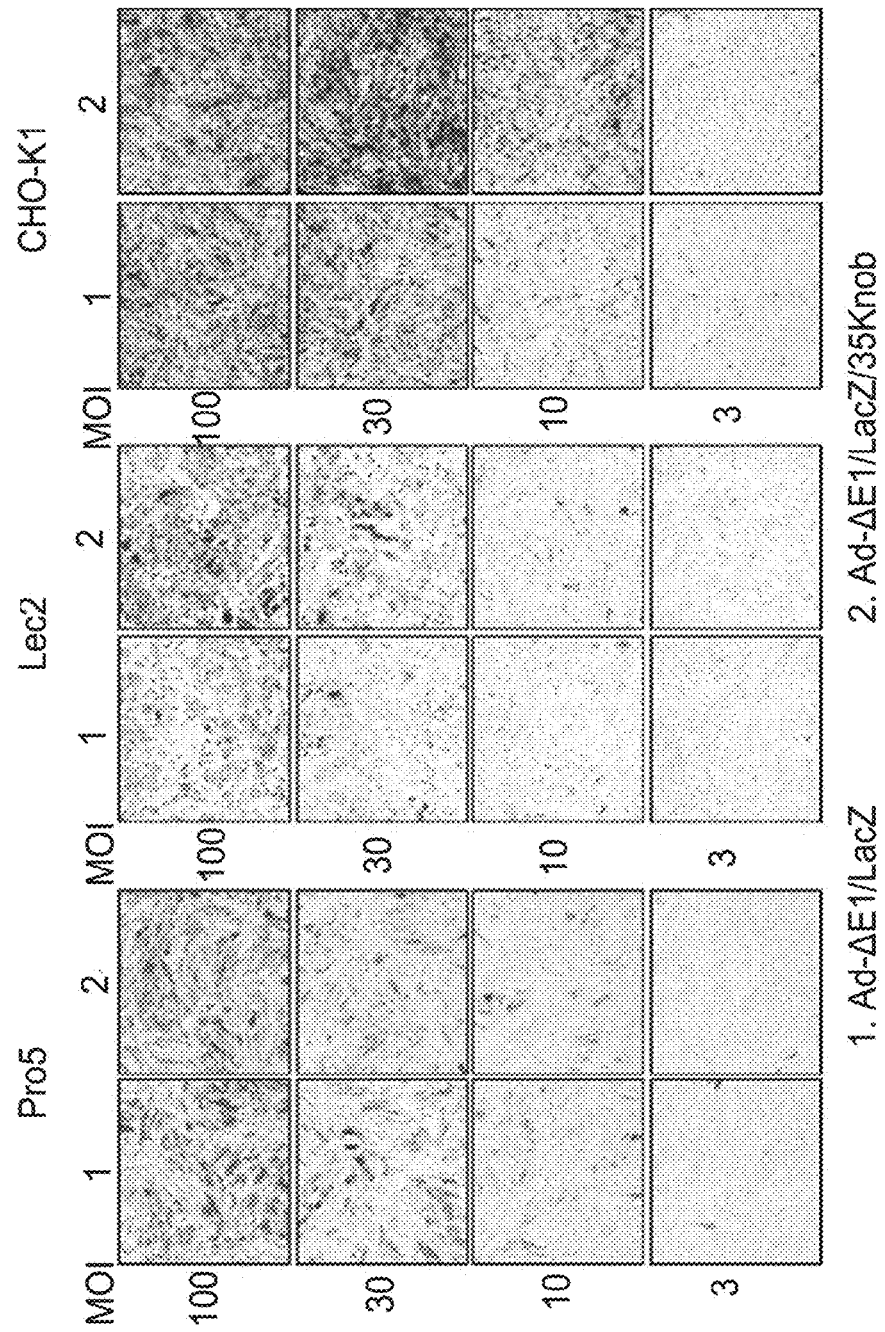
FIG. 21: gene transduction efficiencies according to LacZ expression, after infecting ProS, Lec2 and CHO-K1 cell lines with a control adenovirus (Ad-ΔE1/LacZ) and an adenovirus replaced with serotype 35 fiber (Ad-ΔE1/LacZ/35K).

In order to measure the cancer cell infection activity of the adenovirus prepared in Example <5-1>, various normal and tumor cells were infected with Ad-ΔE1/LacZ and Ad-ΔE1/LacZ/35K. 48 hours after infection, the expression level of LacZ was examined. The results are shown in FIGS. 19 to 21.

Figure 19:
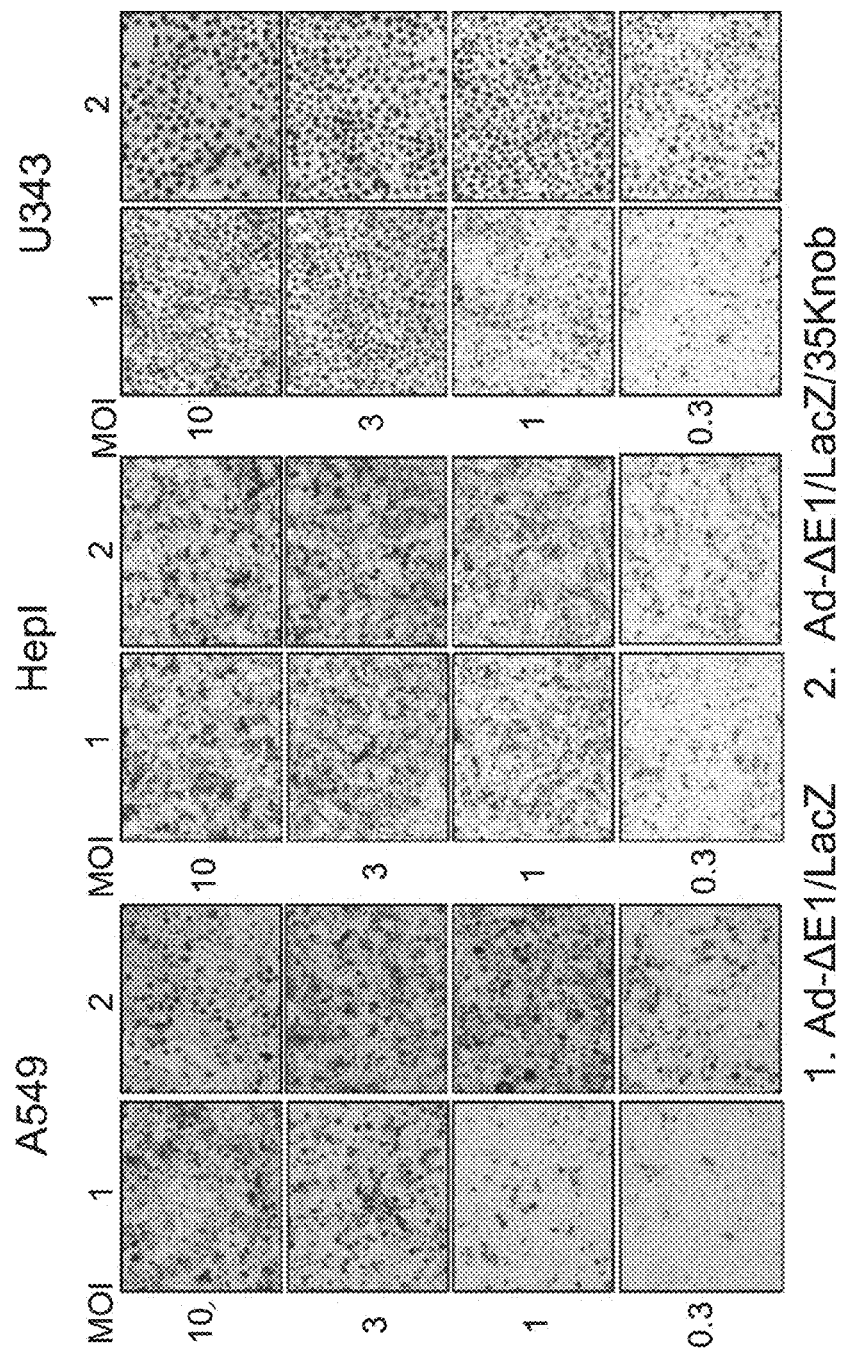
FIG. 19: gene transduction efficiencies according to LacZ expression, after infecting A549, HepI and U343 cell lines with a control adenovirus (Ad-ΔE1/LacZ) and an adenovirus replaced with serotype 35 fiber (Ad-ΔE1/LacZ/35K)

As a result, the gene delivery efficiency increased about 3 times in HepI and U343 cell lines expressing CAR in a high level, and about 10 times in A549 cell lines expressing CAR in a low level (FIG. 19). Further, of the analysis for gene delivery efficiency in cell lines expressing CAR in a low level and normal cell lines reveals that tumor cell lines FaDu and MCF-7, which show low infection rate of adenovirus serotype 5 due to low expression level of CAR, showed increased gene delivery efficiency of about ten times or more by the substitution of the fiber protein of Ad35. The adenovirus substituted with the fiber protein of Ad35 showed increase gene delivery efficiency of about 30 times in CBHEL where the expression level of CAR is low. The results indicate that the adenovirus substituted with Ad35 fiber protein would be effectively available to cell lines or a body having low infection rate to Ad5 adenovirus (FIG. 20).

Finally, CHO-K1, ProS and Lec2 cell lines, which show no expression of CAR, were infected with Ad5 adenovirus and an adenovirus substituted with Ad35 fiber protein, respectively, and the gene delivery efficiency was analyzed. As a result, both adenoviruses showed similar gene delivery efficiencies in ProS cells, but an adenovirus substituted with Ad35 fiber protein showed 3 times higher gene delivery efficiency compared to Ad5 adenovirus in Lec2 and CHO-K1 cells (FIG. 21).

In conclusion, the adenovirus substituted with Ad35 fiber protein showed about 3 to 30 times higher gene delivery efficiency than Ad5 adenovirus in most cell lines, irrespective of the expression of CAR, a cell receptor of adenovirus serotype 5. Therefore, the low infection rate of adenovirus serotype 5 would be overcome by mere substitution of the fiber protein.

What is claimed is:

1. A nucleic acid construct comprising a nucleic acid molecule of the nucleotide sequence consisting of SEQ ID NO: 8 or 10, or a fragment of SEQ ID NO: 10, said fragment exhibiting a tumor-specific promoter activity and an exogenous gene operably linked to the nucleic acid molecule or the fragment of SEQ ID NO: 10.

2. The nucleic acid construct of claim 1, wherein the fragment comprises the nucleotide sequence of SEQ ID NO: 8 and does not exceed the nucleotide sequence of SEQ ID NO: 10.

3. The nucleic acid construct of claim 1, further comprising an additional sequence selected from the group consisting of CMV, SV40, TK, β-actin, eIF4A1, GAPDH, EF1, hsp70, ubiquitin B, albumin, al-antitrypsin protease, FVII, B29, CD14, CD43, CD45, CD68, elastase-1, endoglin, fibronectin, flt-1, GFAP, ICAM-2, E2F1, TERT, PSA, AFP, CEA, survivin, COX-2, CXCR4, and MUC1.

4. An expression vector comprising the nucleic acid construct of claim 1.

5. A viral expression vector which regulates a genomic gene expression of a virus, said vector comprising the nucleic acid construct of claim 1.

6. The viral expression vector of claim 5, wherein the virus is selected from the group consisting of adenovirus, adeno-associated virus, retrovirus, lentivirus, herpes simplex virus, and reovirus.

7. The viral expression vector of claim 5, wherein the virus is an adenovirus derived from primates.

8. The viral expression vector of claim 5, wherein the viral genomic gene is an adenoviral genomic gene selected from the group consisting of E1A, E1B, E2A, E2B, E3, E4, L1, L2, L3, L4, and L5.

9. The viral expression vector of claim 5, wherein the exogenous nucleotide sequence is selected from the group consisting of tumor suppressor genes, cytotoxic genes, cytostatic genes, cytokines, suicide genes, and antigen encoding genes.

10. The viral expression vector of claim 5, wherein a part of the genomic gene of a virus is replaced with another gene.

11. The viral expression vector of claim 8, wherein the E1A gene in the adenoviral genome is replaced with a mutant E1A gene having the nucleotide sequence of SEQ ID NO: 17, or wherein the E1B gene in the adenoviral genome is replaced with an E1B55K where the 19 KDa region of the E1B is deleted.

12. A pharmaceutical composition for treating a cancer, comprising the viral expression vector of claim 5 and a pharmaceutically acceptable carrier.

* * * * *

SEQUENCE LISTING

<160> NUMBER OF SEQ ID NOS: 17

<210> SEQ ID NO 1
<211> LENGTH: 23
<212> TYPE: DNA
<213> ORGANISM: Artificial Sequence

```
<220> FEATURE:
<223> OTHER INFORMATION: Sense primer for human DS promoter

<400> SEQUENCE: 1
cttctcgctg ctttatcccc atc                                          23

<210> SEQ ID NO 2
<211> LENGTH: 21
<212> TYPE: DNA
<213> ORGANISM: Artificial Sequence
<220> FEATURE:
<223> OTHER INFORMATION: Antisense primer for human DS promoter or DL
      promoter

<400> SEQUENCE: 2
ctcggaggct tcagcagacg c                                            21

<210> SEQ ID NO 3
<211> LENGTH: 29
<212> TYPE: DNA
<213> ORGANISM: Artificial Sequence
<220> FEATURE:
<223> OTHER INFORMATION: Sense primer for human E2F promoter

<400> SEQUENCE: 3
cctatgttcc ggtgtcccca cgcctccag                                    29

<210> SEQ ID NO 4
<211> LENGTH: 25
<212> TYPE: DNA
<213> ORGANISM: Artificial Sequence
<220> FEATURE:
<223> OTHER INFORMATION: Antisense primer for human E2F promoter

<400> SEQUENCE: 4
gacgctcacg gcccgcgcgg cccgg                                        25

<210> SEQ ID NO 5
<211> LENGTH: 23
<212> TYPE: DNA
<213> ORGANISM: Artificial Sequence
<220> FEATURE:
<223> OTHER INFORMATION: Sense primer for human DL promoter

<400> SEQUENCE: 5
tcaccatgcc cagcaaatct ttg                                          23

<210> SEQ ID NO 6
<211> LENGTH: 33
<212> TYPE: DNA
<213> ORGANISM: Artificial Sequence
<220> FEATURE:
<223> OTHER INFORMATION: Antisense primer for human 5'E2F promoter

<400> SEQUENCE: 6
ccacttttac gcgccaaatc cttttttgccg cga                              33

<210> SEQ ID NO 7
<211> LENGTH: 23
<212> TYPE: DNA
<213> ORGANISM: Artificial Sequence
<220> FEATURE:
<223> OTHER INFORMATION: Antisense primer for human dDS or dDL promoter

<400> SEQUENCE: 7
atggggaggg gcgatgagcg gag                                          23
```

<210> SEQ ID NO 8
<211> LENGTH: 342
<212> TYPE: DNA
<213> ORGANISM: Artificial Sequence
<220> FEATURE:
<223> OTHER INFORMATION: designed sequence of Tumor specific DS promoter

<400> SEQUENCE: 8

```
cttctcgctg ctttatcccc atcacacctg aaagaatgaa tgaatgaatg cctcgggcac      60
cgtgcccacc tcccagcaaa ccgtggagct tggacgagcc cactgctccg cgtgggggggg    120
gtgtgtgccc gccttgcgca tgcgtgttcc ctgggcatgg ccggctccgt tccatccttc    180
tgcacagggt atcgcctctc tccgtttggt acatcccctc ctcccccacg cccggactgg    240
ggtggtagac gccgcctccg ctcatcgccc ctccccatcg gtttccgcgc gaaaagccgg    300
ggcgcctgcg ctgccgccgc cgcgtctgct gaagcctccg ag                       342
```

<210> SEQ ID NO 9
<211> LENGTH: 411
<212> TYPE: DNA
<213> ORGANISM: Artificial Sequence
<220> FEATURE:
<223> OTHER INFORMATION: designed sequence of Tumor specific E2F
      promoter

<400> SEQUENCE: 9

```
cctatgttcc ggtgtcccca cgcctccagc aggggacgcc cgggctgggg gcggggagtc     60
acaccgcgcc tggtaccatc cggacaaagc ctgcgcgcgc cccgccccgc cattggccgt    120
accgccccgc gccgccgccc catcccgccc ctcgccgccg ggtccggcgc gttaaagcca    180
ataggaaccg ccgccgttgt tcccgtcacg gccggggcag ccaattgtgg cggcgctcgg    240
cggctcgtgg ctctttcgcg gcaaaaagga tttggcgcgt aaaagtggcc gggactttgc    300
aggcagcggc ggccgggggc ggagcgggat cgagccctcg ccgaggcctg ccgccatggg    360
cccgcgccgc cgccgccgcc tgtcacccgg gccgcgcggg ccgtgagcgt c             411
```

<210> SEQ ID NO 10
<211> LENGTH: 1108
<212> TYPE: DNA
<213> ORGANISM: Artificial Sequence
<220> FEATURE:
<223> OTHER INFORMATION: designed sequence of Tumor specific DL promoter

<400> SEQUENCE: 10

```
tcaccatgcc cagcaaatct ttgtattttt tgtagagatg gggtatccct atgttgctca     60
ggctggtctt gaactcctaa cctcaagcga tcctcccacc tgggcctctc aaagcactgg    120
gattacaggc gtgagccact gcgcctgaca tggtgcttct taatttattc ttacttttta    180
tttttatttt tttgagacaa ggtcttgctc tgtctcccag gctggaatgt agtggtacaa    240
tcatggctca ctgcaacctc tgcctctccg gttcaagtga tcttcctgcc tcaacctctg    300
gagtagtttg gactatgggc acatgccaca acgactagct aattttttgtt tttcttttt    360
tctttctttc tttctttctt tttttttttt tttgagatgc agtttctcta tgttacctag    420
gctggtctaa aactcctggg ctcaagcgat cctcccaccc tggcctccca agtgctggg    480
atgacaggcg tgagccacgt ggtgcttaaa aaaggcaaca aaaaccccc cacacactgg    540
gtatagaagt ggcatgggcc tctatacact gtgagattct tggtactagc tacaaattct    600
gtgtatactc aagattttct agagtaggtg caattacccc gttttacaga tgaggacaca    660
```

```
gaggctgagc cgtagtgacc cacctaaggt cgtatagcca gcaaatagat ggaggttgga      720
ttggaactga ggactttact caagggctct cacaaaccct tgggggcttc tcgctgcttt      780
atccccatca cacctgaaag aatgaatgaa tgaatgcctc gggcaccgtg cccacctccc      840
agcaaaccgt ggagcttgga cgagcccact gctccgcgtg ggggggtgt gtgcccgcct       900 tgcgcatgcg tgttccctgg gcatggccgg ctccgttcca tccttctgca cagggtatcg      960
cctctctccg tttggtacat cccctcctcc ccacgcccg gactgggtg gtagacgccg       1020 cctccgctca tcgcccctcc ccatcggttt ccgcgcgaaa agccggggcg cctgcgctgc     1080
cgccgccgcg tctgctgaag cctccgag                                       1108
```

```
<210> SEQ ID NO 11
<211> LENGTH: 288
<212> TYPE: DNA
<213> ORGANISM: Artificial Sequence
<220> FEATURE:
<223> OTHER INFORMATION: designed sequence of Tumor specific 5'E2F
      promoter

<400> SEQUENCE: 11
cctatgttcc ggtgtcccca cgcctccagc aggggacgcc cgggctgggg gcggggagtc       60
acaccgcgcc tggtaccatc cggacaaagc ctgcgcgcgc cccgccccgc cattggccgt      120
accgccccgc gccgccgccc catcccgccc ctcgccgccg gtccggcgc gttaaagcca       180 ataggaaccg ccgccgttgt tcccgtcacg gccggggcag ccaattgtgg cggcgctcgg      240
cggctcgtgg ctctttcgcg gcaaaaagga tttggcgcgt aaaagtgg                  288
```

```
<210> SEQ ID NO 12
<211> LENGTH: 692
<212> TYPE: DNA
<213> ORGANISM: Artificial Sequence
<220> FEATURE:
<223> OTHER INFORMATION: Tumor specific 5'ED promoter

<400> SEQUENCE: 12
cctatgttcc ggtgtcccca cgcctccagc aggggacgcc cgggctgggg gcggggagtc       60
acaccgcgcc tggtaccatc cggacaaagc ctgcgcgcgc cccgccccgc cattggccgt      120
accgccccgc gccgccgccc catcccgccc ctcgccgccg gtccggcgc gttaaagcca       180 ataggaaccg ccgccgttgt tcccgtcacg gccggggcag ccaattgtgg cggcgctcgg      240
cggctcgtgg ctctttcgcg gcaaaaagga tttggcgcgt aaaagtggaa gggcgaattc      300
tgcagatatc catcacactg gcggccgctc gacgcgtaga attcgccctt cttctcgctg      360
ctttatcccc atcacacctg aaagaatgaa tgaatgaatg cctcgggcac cgtgcccacc      420
tcccagcaaa ccgtggagct tggacgagcc cactgctccg cgtggggggg gtgtgtgccc      480
gccttgcgca tgcgtgttcc ctgggcatgg ccggctccgt tccatccttc tgcacagggt      540
atcgcctctc tccgtttggt acatcccctc ctccccacg cccggactgg ggtggtagac      600
gccgcctccg ctcatcgccc ctccccatcg gtttccgcgc gaaaagccgg ggcgcctgcg      660
ctgccgccgc gcgtctgct gaagcctccg ag                                    692
```

```
<210> SEQ ID NO 13
<211> LENGTH: 278
<212> TYPE: DNA
<213> ORGANISM: Artificial Sequence
<220> FEATURE:
<223> OTHER INFORMATION: designed sequence of Tumor specific dDS
``` promoter

<400> SEQUENCE: 13

| | |
|---|---|
| cttctcgctg ctttatcccc atcacacctg aaagaatgaa tgaatgaatg cctcgggcac | 60 |
| cgtgcccacc tcccagcaaa ccgtggagct tggacgagcc cactgctccg cgtgggggg | 120 |
| gtgtgtgccc gccttgcgca tgcgtgttcc ctgggcatgg ccggctccgt tccatccttc | 180 |
| tgcacagggt atcgcctctc tccgtttggt acatcccctc ctcccccacg cccggactgg | 240 |
| ggtggtagac gccgcctccg ctcatcgccc ctccccat | 278 |

<210> SEQ ID NO 14
<211> LENGTH: 1044
<212> TYPE: DNA
<213> ORGANISM: Artificial Sequence
<220> FEATURE:
<223> OTHER INFORMATION: designed sequence of Tumor specific dDL promoter

<400> SEQUENCE: 14

| | |
|---|---|
| tcaccatgcc cagcaaatct ttgtattttt tgtagagatg gggtatccct atgttgctca | 60 |
| ggctggtctt gaactcctaa cctcaagcga tcctcccacc tgggcctctc aaagcactgg | 120 |
| gattacaggc gtgagccact gcgcctgaca tggtgcttct taatttattc ttactttta | 180 |
| ttttattt tttgagacaa ggtcttgctc tgtctcccag gctggaatgt agtggtacaa | 240 |
| tcatggctca ctgcaacctc tgcctctccg gttcaagtga tcttcctgcc tcaacctctg | 300 |
| gagtagtttg gactatgggc acatgccaca acgactagct aatttttgtt tttcttttt | 360 |
| tctttctttc tttctttctt tttttttttt tttgagatgc agtttctcta tgttacctag | 420 |
| gctggtctaa aactcctggg ctcaagcgat cctcccaccc tggcctccca aagtgctggg | 480 |
| atgacaggcg tgagccacgt ggtgcttaaa aaaggcaaca aaaaacccccc cacacactgg | 540 |
| gtatagaagt ggcatgggcc tctatacact gtgagattct tggtactagc tacaaattct | 600 |
| gtgtatactc aagatttct agagtaggtg caattacccc gttttacaga tgaggacaca | 660 |
| gaggctgagc cgtagtgacc cacctaaggt cgtatagcca gcaaatagat ggaggttgga | 720 |
| ttggaactga ggacttttact caagggctct cacaaaccct tggggcttc tcgctgcttt | 780 |
| atccccatca cacctgaaag aatgaatgaa tgaatgcctc gggcaccgtg cccacctccc | 840 |
| agcaaaccgt ggagcttgga cgagcccact gctccgcgtg ggggggtgt gtgcccgcct | 900 |
| tgcgcatgcg tgttccctgg gcatggccgg ctccgttcca tccttctgca cagggtatcg | 960 |
| cctctctccg tttggtacat cccctcctcc cccacgcccg gactggggtg gtagacgccg | 1020 |
| cctccgctca tcgcccctcc ccat | 1044 |

<210> SEQ ID NO 15
<211> LENGTH: 25
<212> TYPE: RNA
<213> ORGANISM: Artificial Sequence
<220> FEATURE:
<223> OTHER INFORMATION: synthetic construct of E2F-1 siRNA

<400> SEQUENCE: 15

| | |
|---|---|
| cccuuaagag caaacaaggc ccgau | 25 |

<210> SEQ ID NO 16
<211> LENGTH: 25
<212> TYPE: RNA
<213> ORGANISM: Artificial Sequence
<220> FEATURE:
<223> OTHER INFORMATION: synthetic construct of beta-catenin siRNA

```
<400> SEQUENCE: 16
ggccugguuu gauacugacc uguaa                                            25

<210> SEQ ID NO 17
<211> LENGTH: 986
<212> TYPE: DNA
<213> ORGANISM: Artificial Sequence
<220> FEATURE:
<223> OTHER INFORMATION: designed sequence of muatant E1A

<400> SEQUENCE: 17
atgagacata ttatctgcca cggaggtgtt attaccgaag aaatggccgc cagtcttttg      60
gaccagctga tcgaagaggt actggctgat aatcttccac ctcctagcca ttttgaacca    120
cctacccttc acggactgta tgatttagac gtgacggccc ccgaagatcc caacgaggag    180
gcggtttcgc agatttttcc cgactctgta atgttggcgg tgcaggaagg gattgactta    240 ctcactttc cgccggcgcc cggttctccg gagccgcctc acctttcccg gcagcccgag     300
cagccggagc agagagcctt gggtccggtt tctatgccaa accttgtacc ggaggtgatc    360
ggtggtggcg gaggcggggg tggctttcca cccagtgacg acgaggatga agagggtgag    420
gagtttgtgt tagattatgt ggagcacccc gggcacggtt gcaggtcttg tcattatcac    480
cggaggaata cggggaccc agatattatg tgttcgcttt gctatatgag gacctgtggc     540
atgtttgtct acagtaagtg aaaattatgg gcagtgggtg atagagtggt gggtttggtg    600 tggtaattt ttttttaatt tttacagttt tgtggtttaa agaattttgt attgtgattt     660
ttttaaaagg tcctgtgtct gaacctgagc ctgagcccga gccagaaccg gagcctgcaa    720
gacctacccg ccgtcctaaa atggcgcctc ctatcctgag acgcccgaca tcacctgtgt    780
ctagagaatg caatagtagt acggatagct gtgactccgg tccttctaac acacctcctg    840
agatacaccc ggtggtcccg ctgtgcccca ttaaaccagt tgccgtgaga gttggtgggc    900
gtcgccaggc tgtggaatgt atcgaggact tgcttaacga gcctgggcaa cctttggact    960
tgagctgtaa acgccccagg ccataa                                          986
```